United States Patent
Ito et al.

(10) Patent No.: US 11,771,335 B2
(45) Date of Patent: Oct. 3, 2023

(54) BIO-OPTICAL MEASURING APPARATUS

(71) Applicant: SONY CORPORATION, Tokyo (JP)

(72) Inventors: Atsushi Ito, Kanagawa (JP); Tomoya Ikuta, Kanagawa (JP)

(73) Assignee: Sony Corporation, Tokyo (JP)

( * ) Notice: Subject to any disclaimer, the term of this patent is extended or adjusted under 35 U.S.C. 154(b) by 644 days.

(21) Appl. No.: 16/639,240

(22) PCT Filed: Jul. 19, 2018

(86) PCT No.: PCT/JP2018/027120
§ 371 (c)(1),
(2) Date: Feb. 14, 2020

(87) PCT Pub. No.: WO2019/039147
PCT Pub. Date: Feb. 28, 2019

(65) Prior Publication Data
US 2020/0205677 A1    Jul. 2, 2020

(30) Foreign Application Priority Data
Aug. 23, 2017    (JP) ................................. 2017-159972

(51) Int. Cl.
*A61B 5/026* (2006.01)
*A61B 5/00* (2006.01)
*A61B 5/0285* (2006.01)

(52) U.S. Cl.
CPC .......... *A61B 5/0261* (2013.01); *A61B 5/0285* (2013.01); *A61B 5/7203* (2013.01); *A61B 2562/0238* (2013.01); *A61B 2562/185* (2013.01)

(58) Field of Classification Search
CPC ...... A61B 2562/0238; A61B 2562/185; A61B 5/0075; A61B 5/0261; A61B 5/0285; A61B 5/7203; A61B 5/7214; A61B 5/7257
See application file for complete search history.

(56) References Cited

U.S. PATENT DOCUMENTS

| | | |
|---|---|---|
| 2012/0130215 A1 | 5/2012 | Fine et al. |
| 2016/0058300 A1 | 3/2016 | Yoon et al. |
| 2019/0293557 A1* | 9/2019 | Sato ..................... A61B 5/7203 |

FOREIGN PATENT DOCUMENTS

| | | |
|---|---|---|
| JP | H05-015501 | 1/1993 |
| JP | H08-182658 | 7/1996 |
| JP | H10-290791 | 11/1998 |
| JP | 2008-011914 | 1/2008 |
| JP | 2012-210321 | 11/2012 |
| JP | 2014-500751 | 1/2014 |

OTHER PUBLICATIONS

International Search Report prepared by the Japan Patent Office dated Sep. 10, 2018, for International Application No. PCT/JP2018/027120.

* cited by examiner

*Primary Examiner* — Amelie R Davis
(74) *Attorney, Agent, or Firm* — SHERIDAN ROSS P.C.

(57) ABSTRACT

A bio-optical measuring apparatus according to an embodiment of the present disclosure includes a light source that emits coherent light; and three or more optical receivers that receive reflected light from a living body, of light outputted from the light source toward the living body. The bio-optical measuring apparatus further includes a signal processing unit that obtains a low-noise signal by performing averaging processing based on detection signals outputted from the respective optical receivers in response to reception of the reflected light.

16 Claims, 19 Drawing Sheets

[ FIG. 1 ]
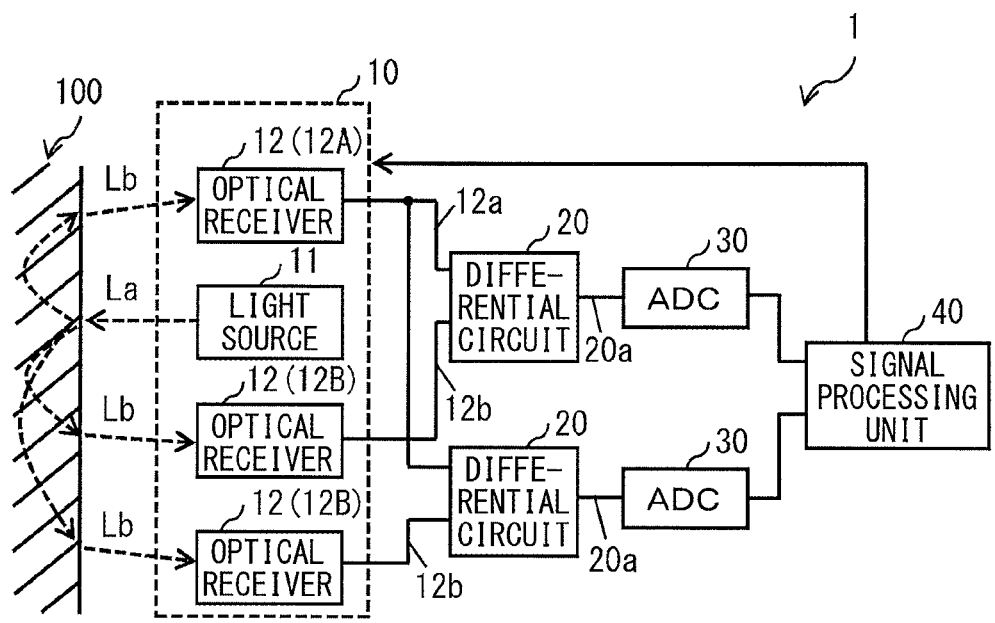
[ FIG. 2 ]
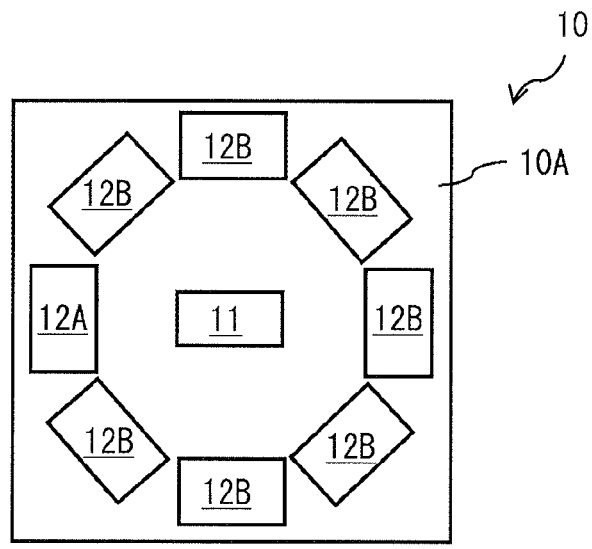

[ FIG. 3 ]
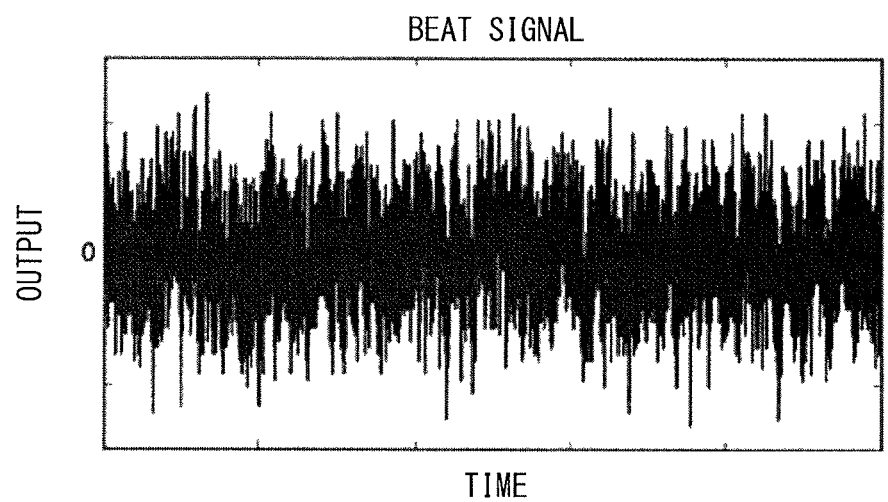
[ FIG. 4 ]
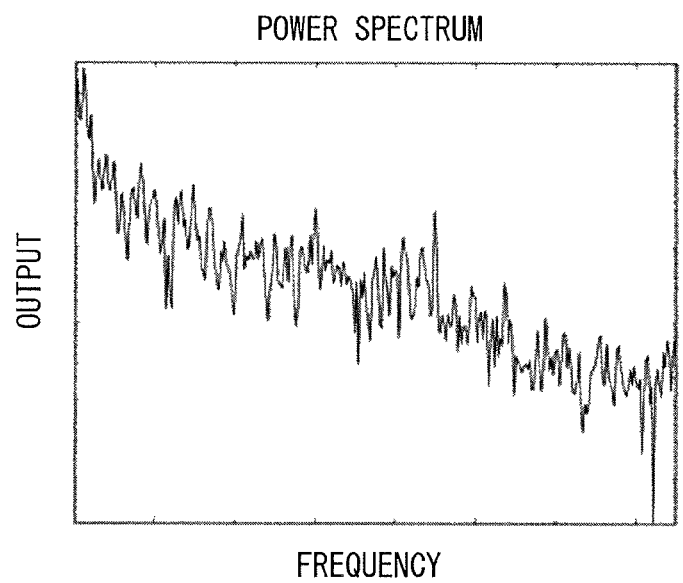

[ FIG. 5 ]
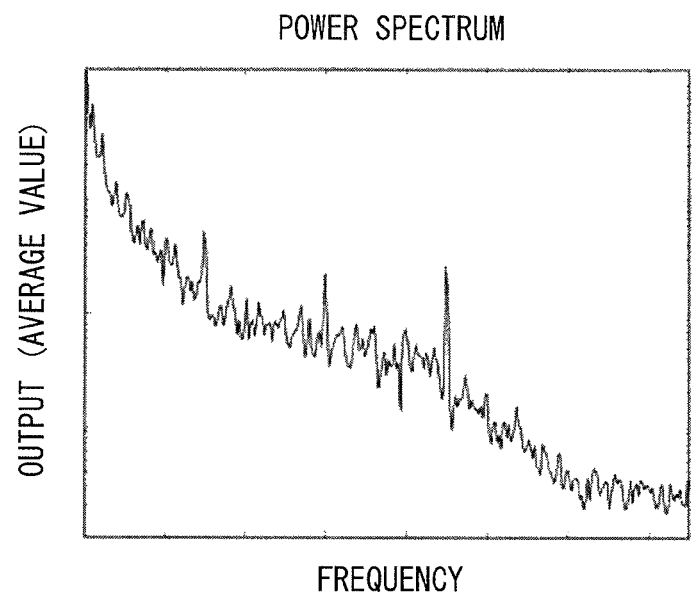
[ FIG. 6 ]
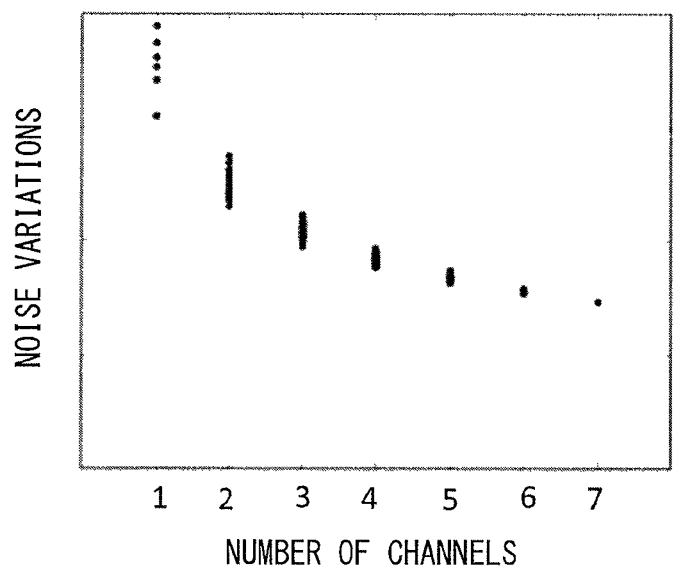

[ FIG. 7 ]
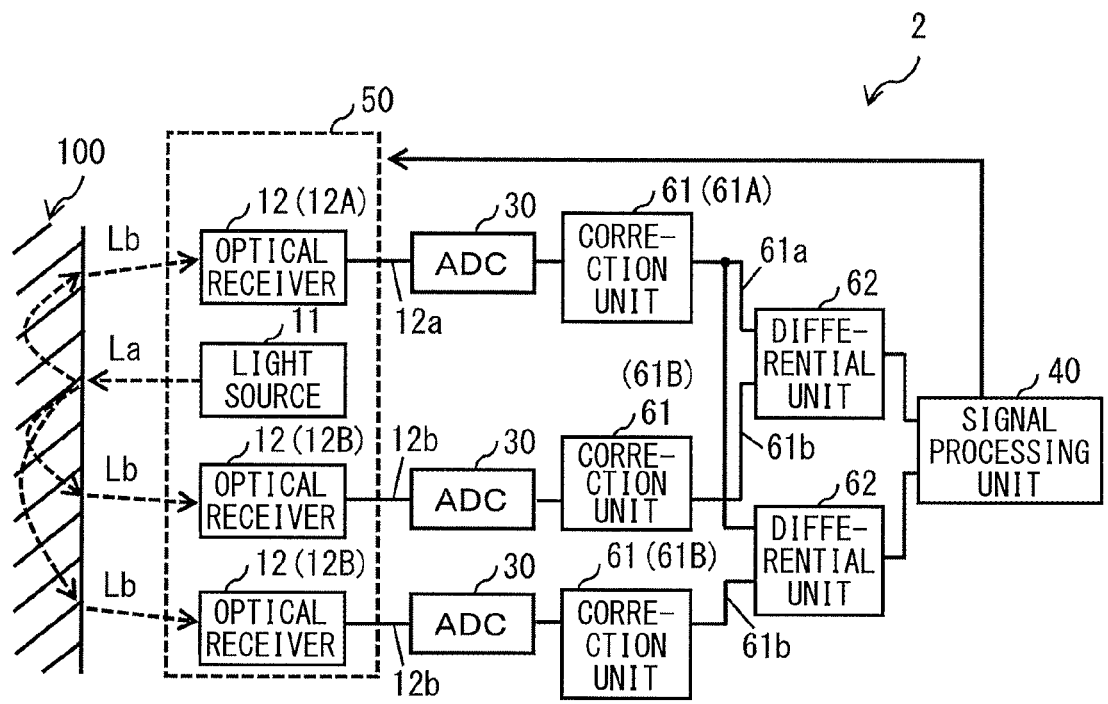
[ FIG. 8 ]
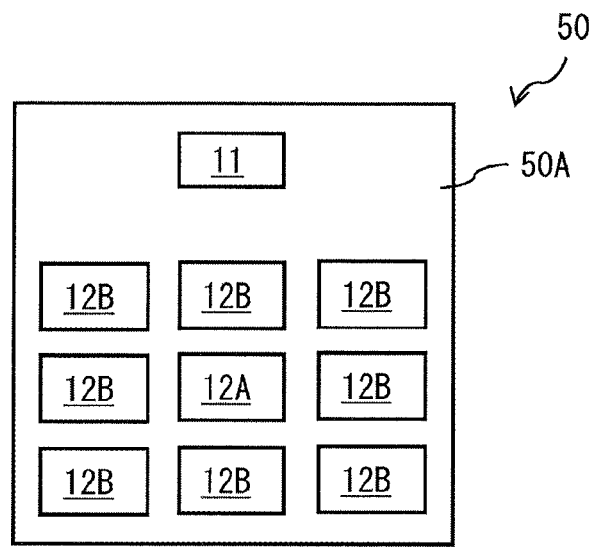

[ FIG. 9 ]
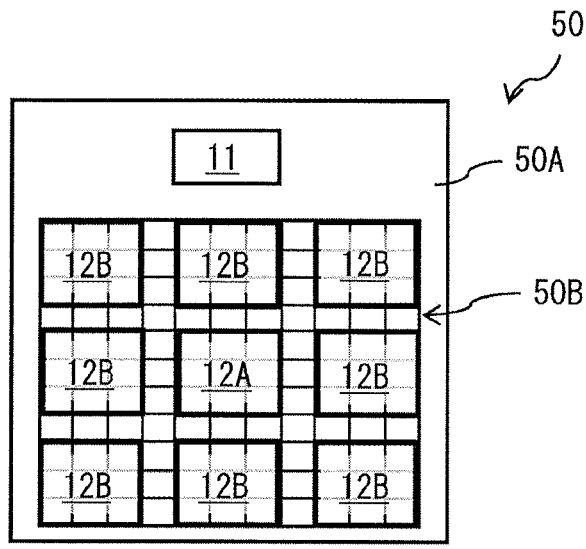
[ FIG. 10 ]
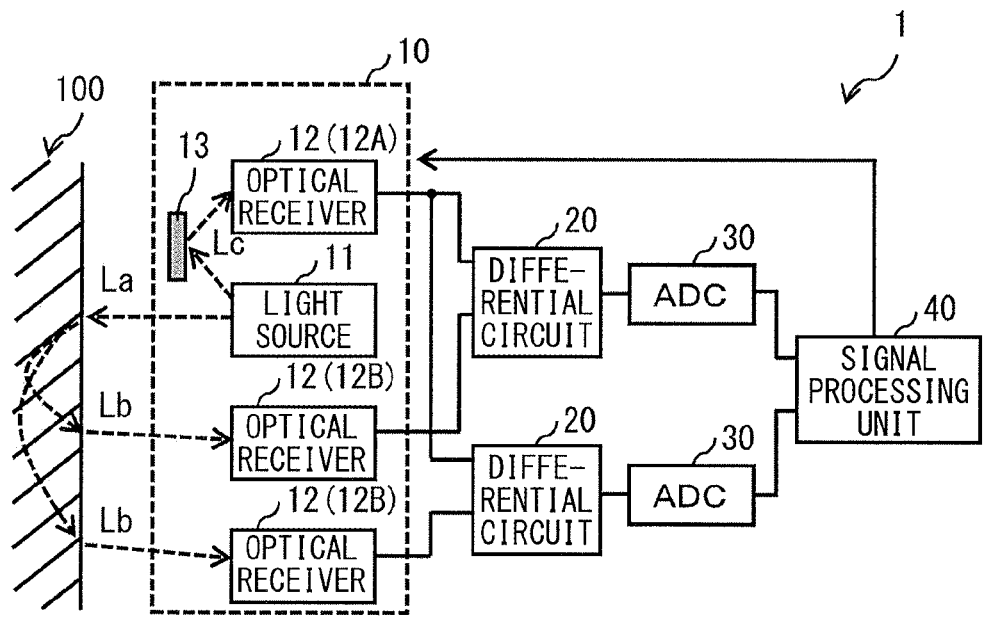

[ FIG. 11 ]
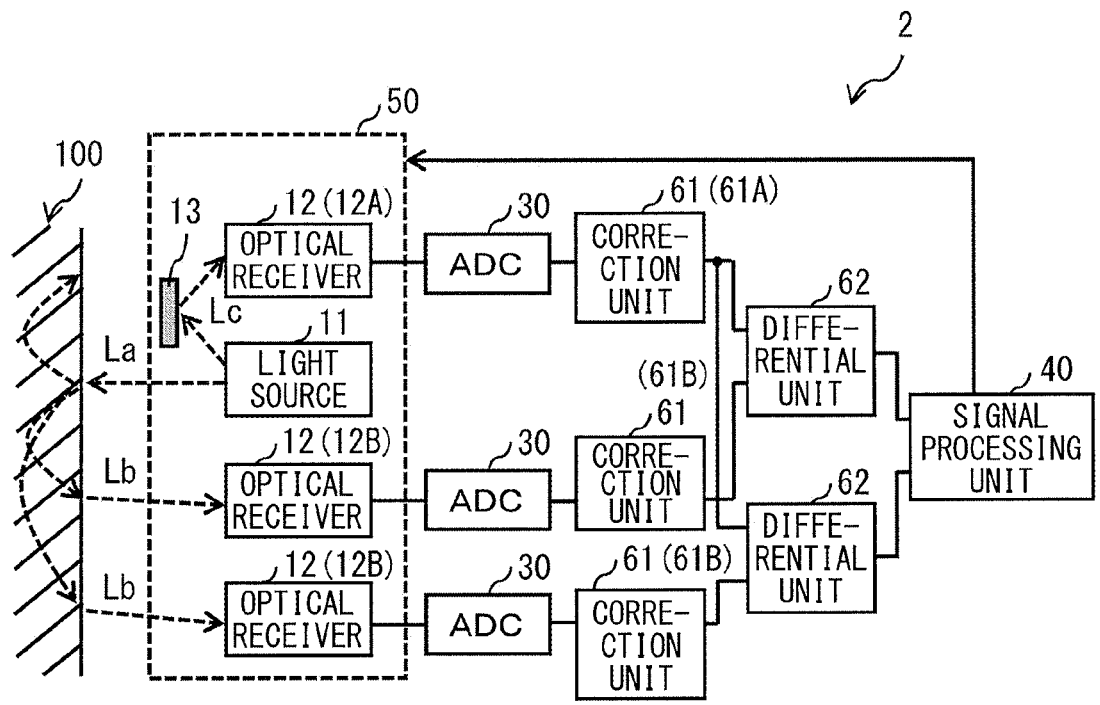
[ FIG. 12 ]
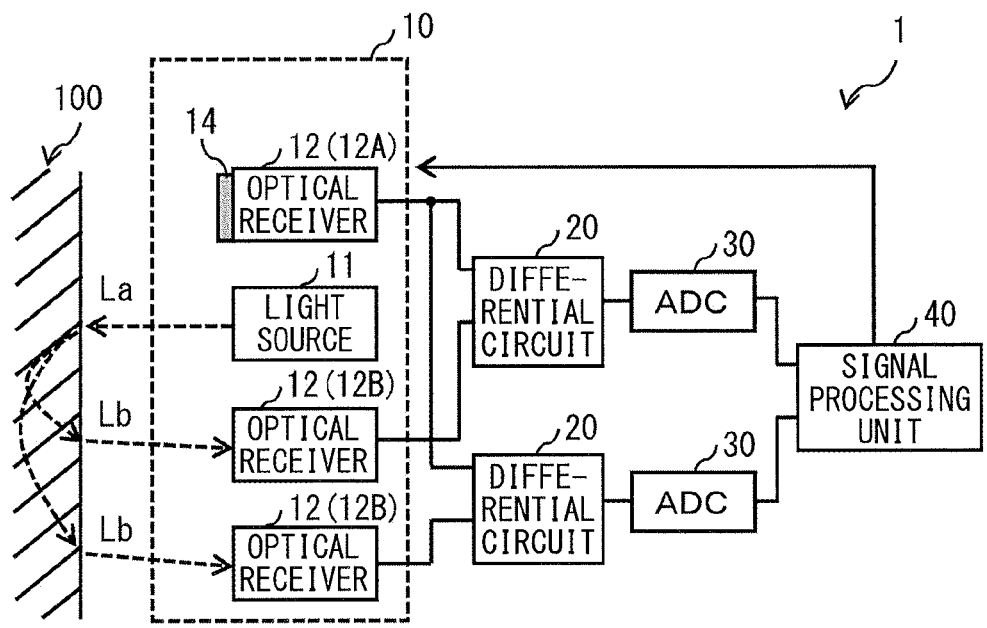

[ FIG. 13 ]
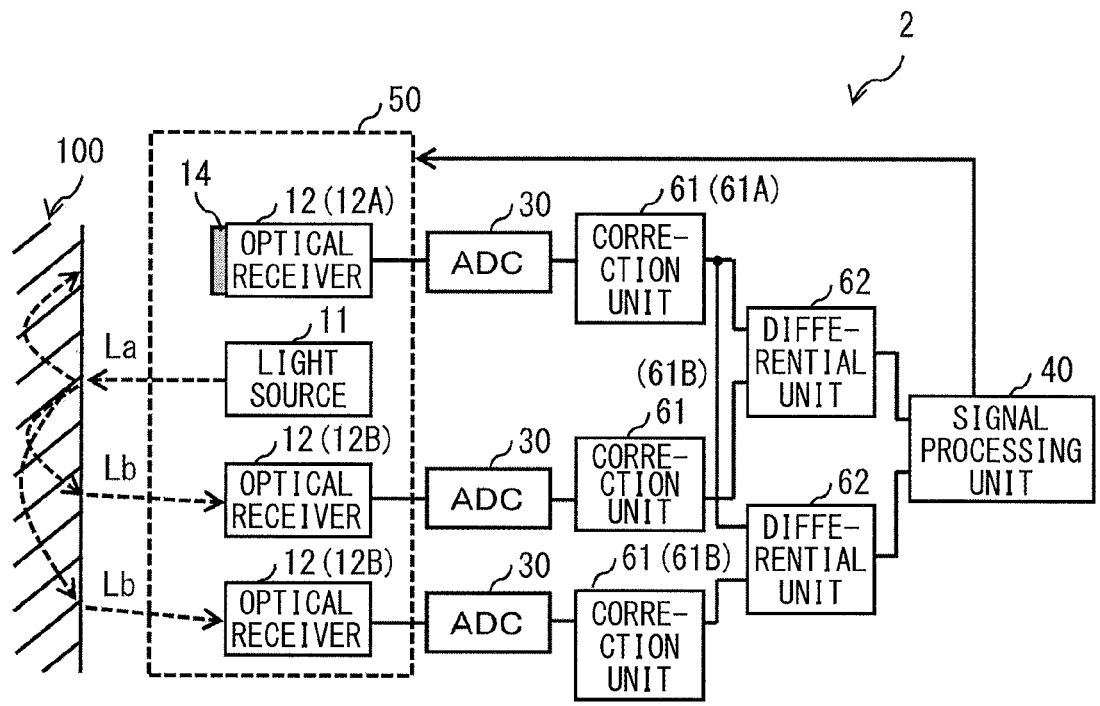
[ FIG. 14 ]
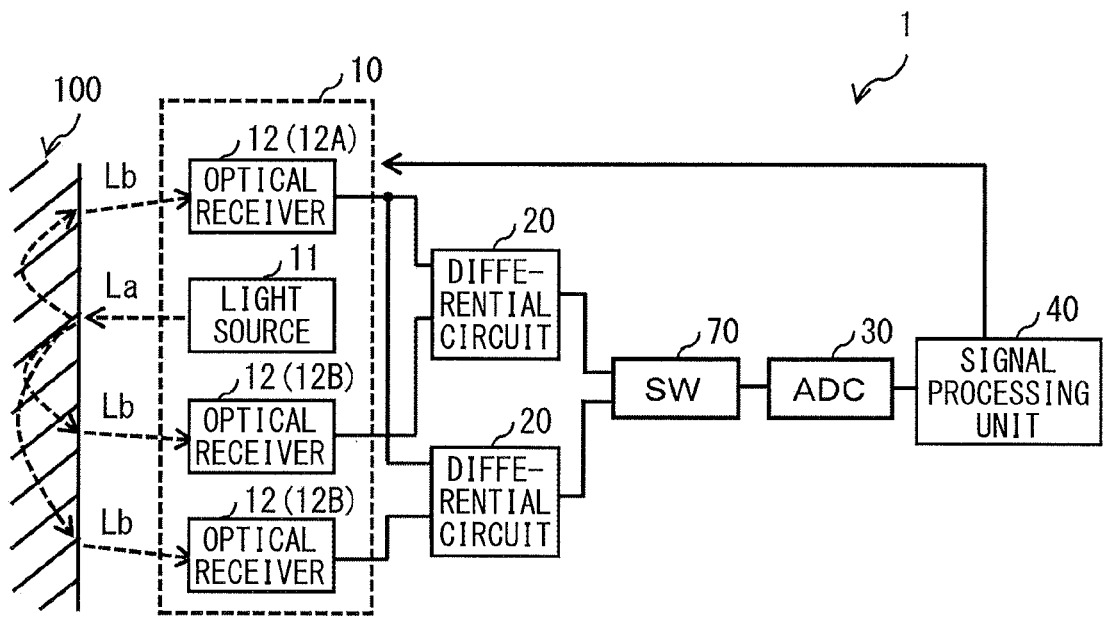

[ FIG. 15 ]
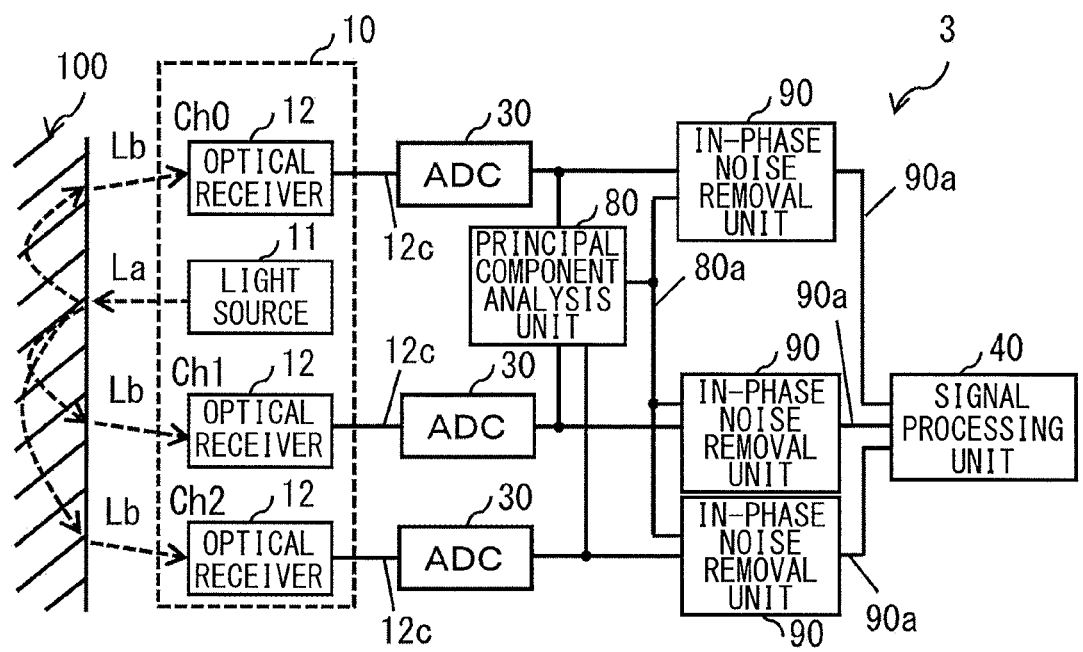
[ FIG. 16 ]
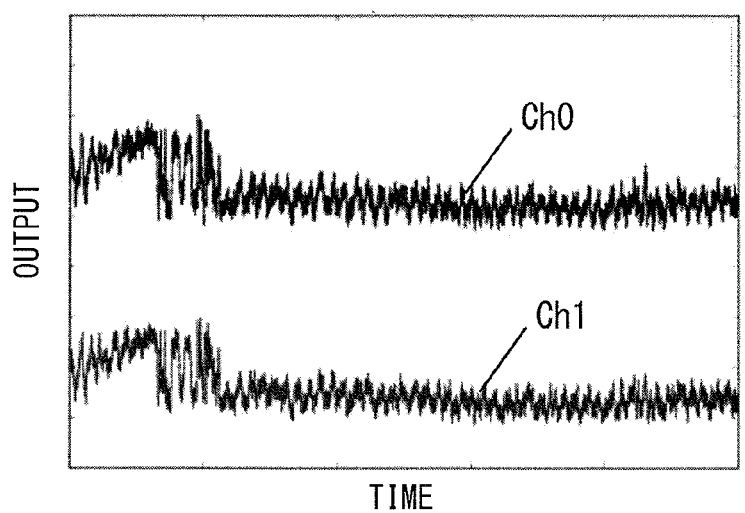

[ FIG. 17 ]
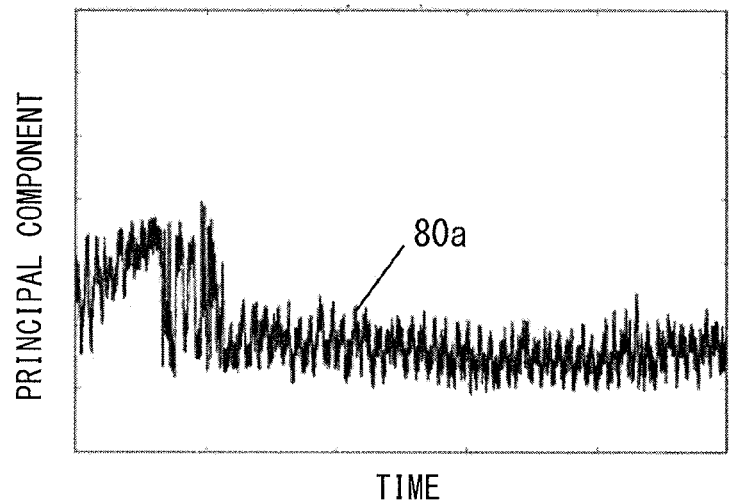
[ FIG. 18 ]
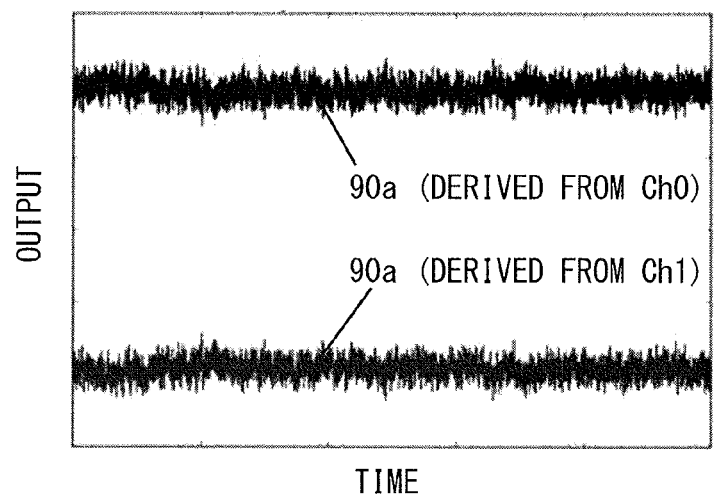

[ FIG. 19 ]
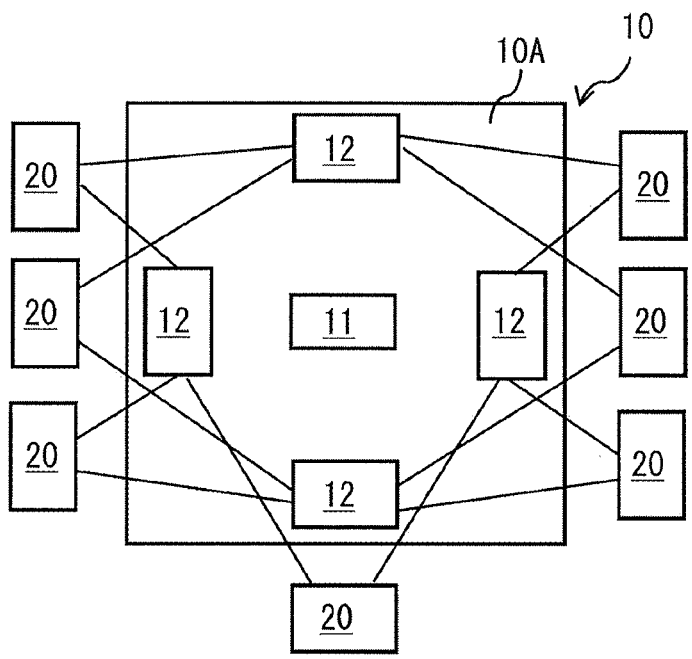
[ FIG. 20 ]
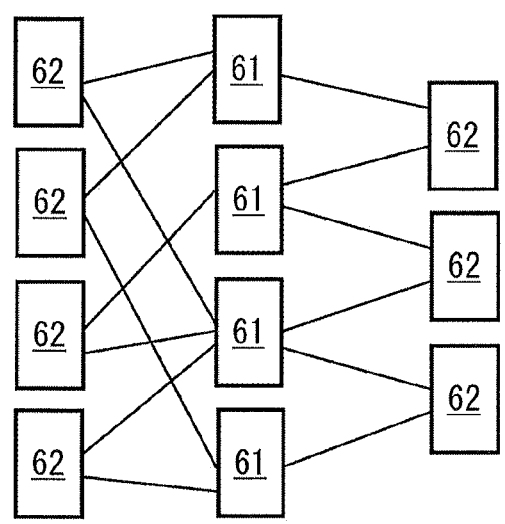

[ FIG. 21 ]
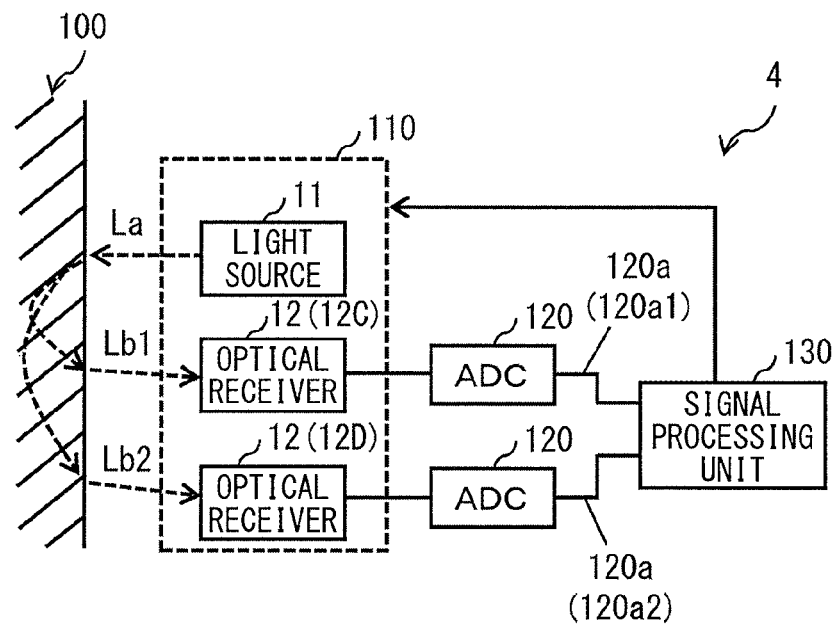
[ FIG. 22 ]
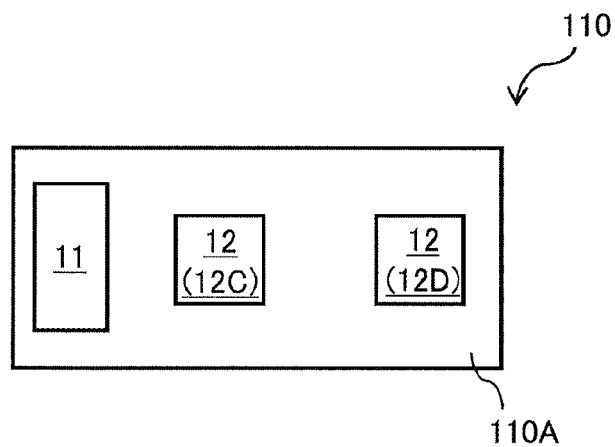

[ FIG. 23 ]
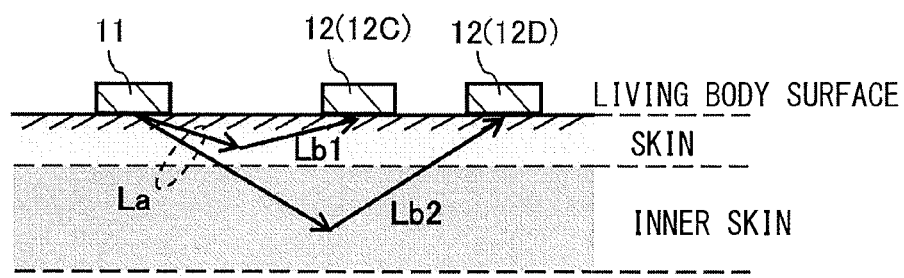
[ FIG. 24 ]
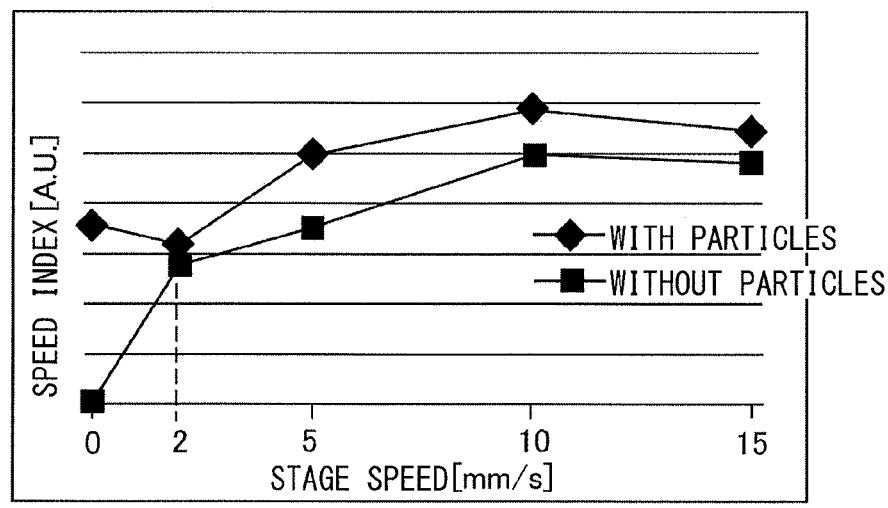

[ FIG. 25 ]
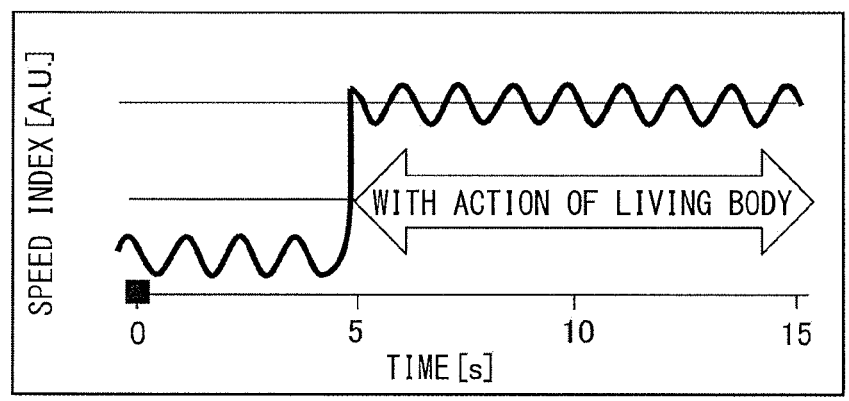
[ FIG. 26 ]
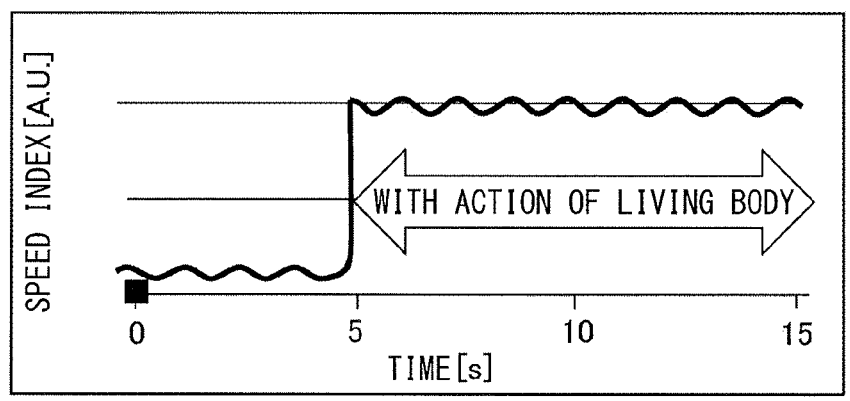

[ FIG. 27 ]
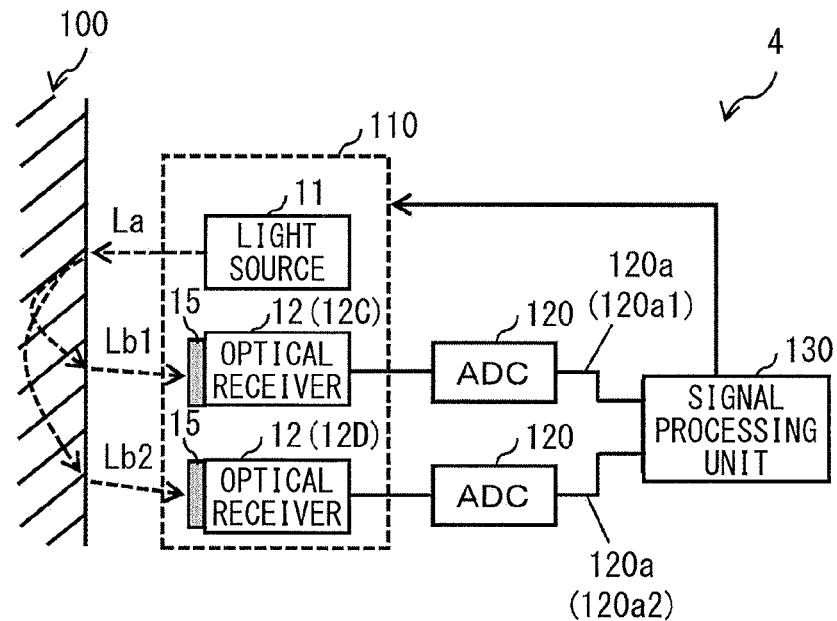
[ FIG. 28 ]
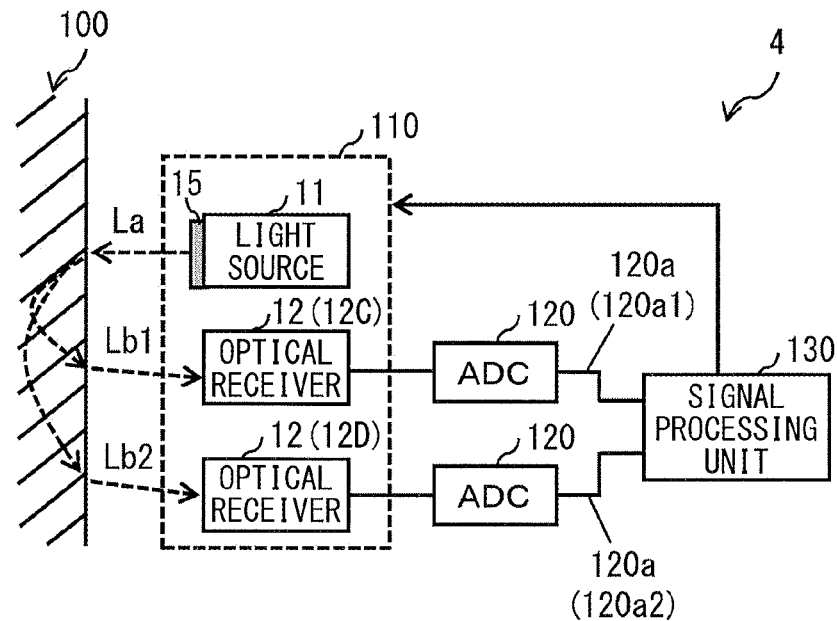

[ FIG. 29 ]
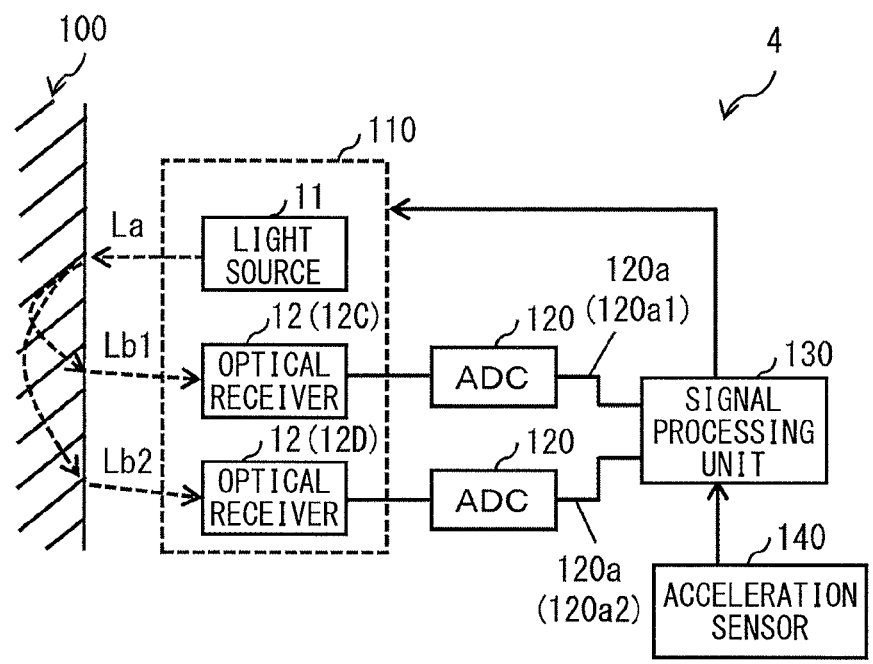

[ FIG. 30 ]
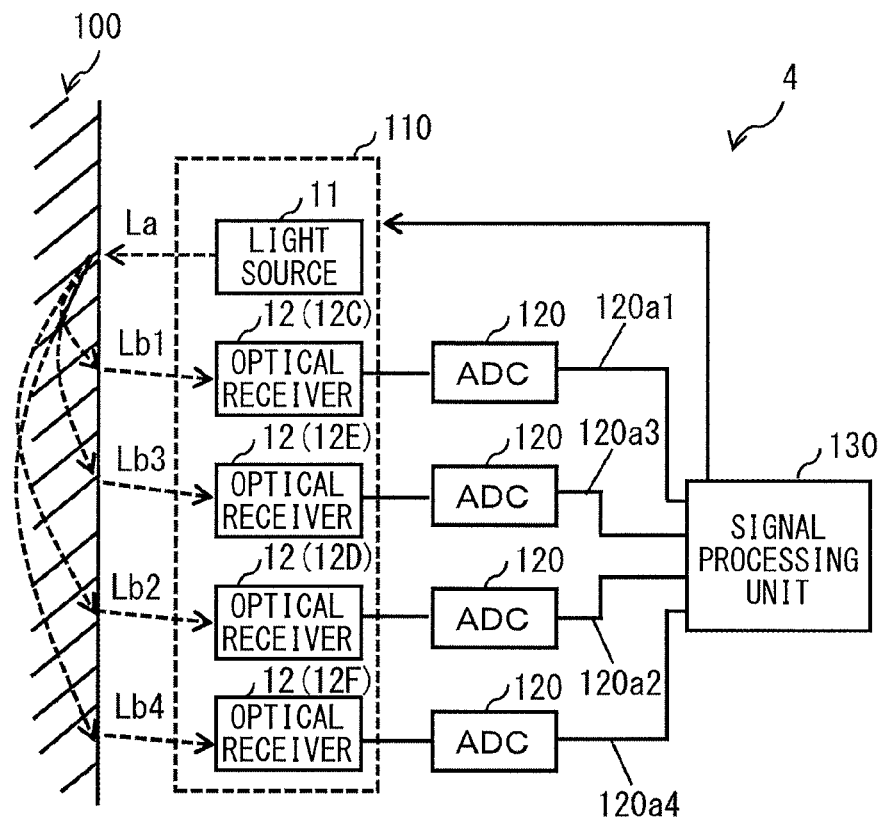
[ FIG. 31 ]
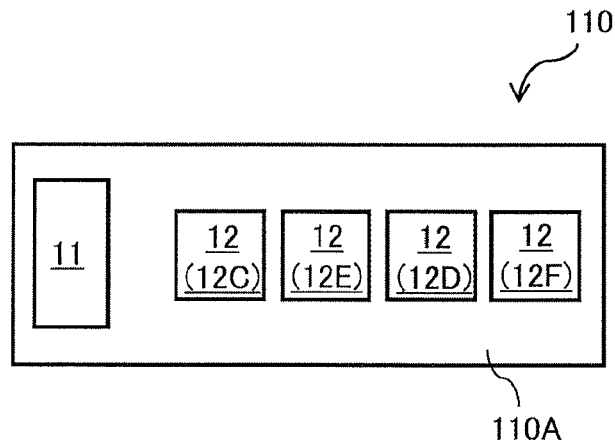

[ FIG. 32 ]
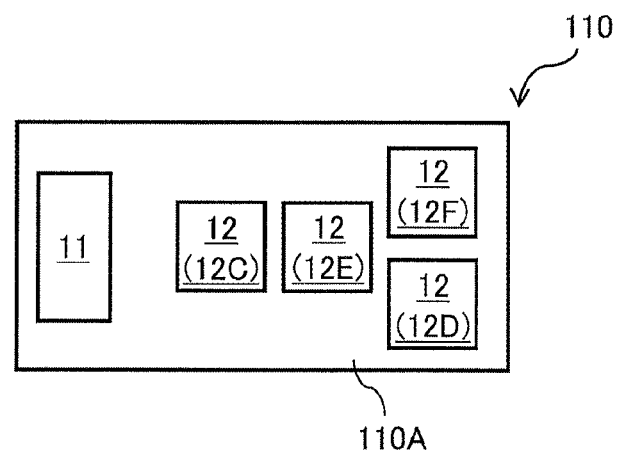

[ FIG. 33 ]
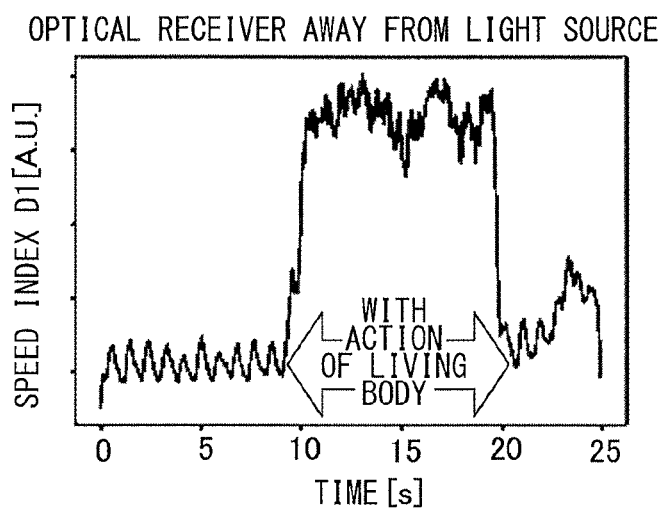
[ FIG. 34 ]
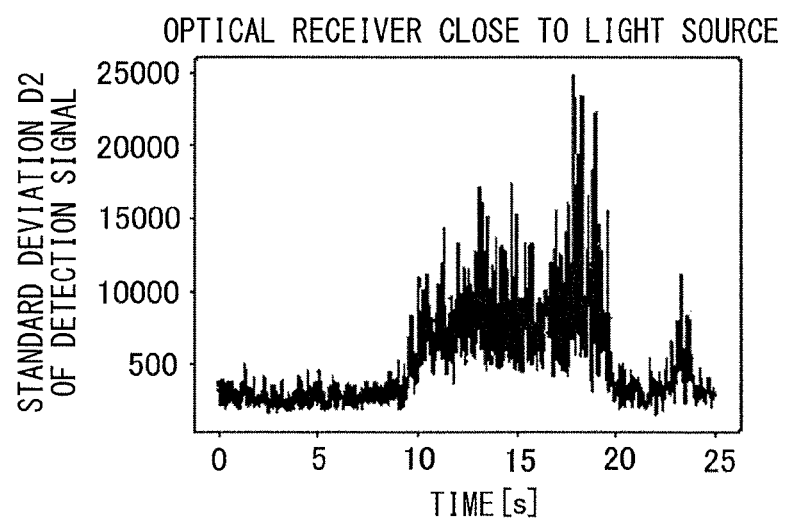

[ FIG. 35 ]
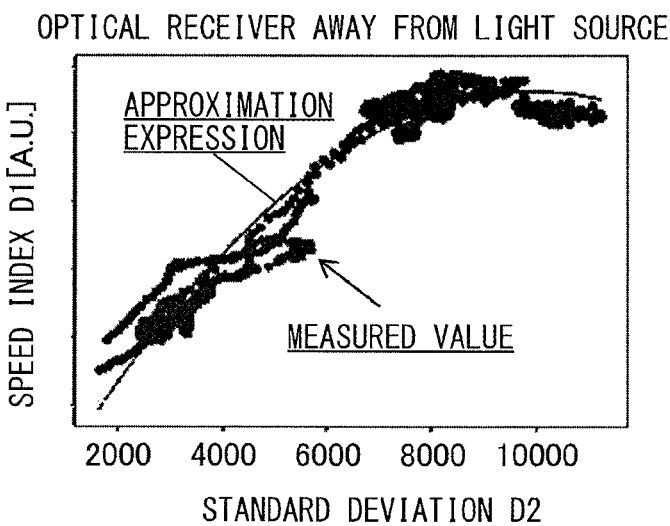
[ FIG. 36 ]
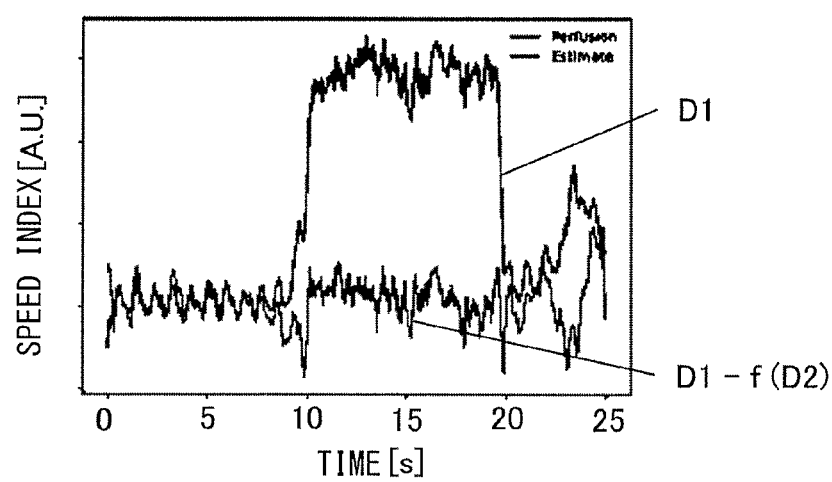

BIO-OPTICAL MEASURING APPARATUS

CROSS REFERENCE TO RELATED APPLICATIONS

This application is a national stage application under 35 U.S.C. 371 and claims the benefit of PCT Application No. PCT/JP2018/027120 having an international filing date of 19 Jul. 2018, which designated the United States, which PCT application claimed the benefit of Japanese Patent Application No. 2017-159972 filed 23 Aug. 2017, the entire disclosures of each of which are incorporated herein by reference.

TECHNICAL FIELD

The present disclosure relates to a bio-optical measuring apparatus.

BACKGROUND ART

There has been a technology called a laser Doppler blood-flowmeter that noninvasively measures a blood flow rate under the skin by irradiating the human skin with coherent light and analyzing backscattered light thereof. The technology has already been commercially available as a measuring instrument. The laser Doppler blood-flowmeter is disclosed in PTLs 1 to 3, for example.

CITATION LIST

Patent Literature

PTL 1: Japanese Unexamined Patent Application Publication No. 2012-210321
PTL 2: Japanese Unexamined Patent Application Publication No. H10-290791
PTL 3: Japanese Unexamined Patent Application Publication No. 2008-11914

SUMMARY OF THE INVENTION

In such a measuring instrument, signal perturbation is caused by a variety of noise, which thus leads to a demand for highly accurate noise removal. Therefore, it is desirable to provide a bio-optical measuring apparatus that is able to perform the highly accurate noise removal.

A first bio-optical measuring apparatus according to an embodiment of the present disclosure includes a light source that emits coherent light; and three or more optical receivers that receive reflected light from a living body, of light outputted from the light source toward the living body. The first bio-optical measuring apparatus further includes a signal processing circuit that obtains a low-noise signal by performing averaging processing based on a detection signal outputted from each of the optical receivers in response to reception of the reflected light.

In the first bio-optical measuring apparatus according to the embodiment of the present disclosure is performed the averaging processing based on the detection signal outputted from each of the optical receivers in response to the reception of the reflected light. This makes it possible to perform the highly accurate noise removal.

A second bio-optical measuring apparatus according to an embodiment of the present disclosure includes a light source that emits coherent light; two or more first optical receivers that receive first reflected light from a living body, of the light outputted from the light source toward the living body; a reflective plate that reflects the light outputted from the light source; and a second optical receiver that receives second reflected light reflected by the reflective plate, of the light outputted from the light source. The second bio-optical measuring apparatus further includes a signal processing circuit that obtains a low-noise signal by performing averaging processing based on a first detection signal outputted from each of the first optical receivers in response to reception of the first reflected light and a second detection signal outputted from the second optical receiver in response to reception of the second reflected light.

In the second bio-optical measuring apparatus according to the embodiment of the present disclosure, the averaging processing based on the first detection signal and the second detection signal is performed. The first detection signal is outputted from each of the first optical receivers in response to the reception of the first reflected light. The second detection signal is outputted from the second optical receiver in response to the reception of the second reflected light. This makes it possible to perform the highly accurate noise removal.

A third bio-optical measuring apparatus according to an embodiment of the present disclosure includes a light source that emits coherent light; two or more first optical receivers that receive first reflected light from a living body, of the light outputted from the light source toward the living body; a light-shielding plate that blocks transmission of the light outputted from the light source; and a second optical receiver into which entry of light from the light source is blocked by the light-shielding plate. The third bio-optical measuring apparatus further includes a signal processing circuit that obtains a low-noise signal by performing averaging processing based on a first detection signal outputted from each of the first optical receivers in response to reception of the reflected light and a second detection signal outputted from the second optical receiver.

In the third bio-optical measuring apparatus according to the embodiment of the present disclosure is performed the averaging processing based on the first detection signal outputted from each of the first optical receivers in response to reception of the reflected light and the second detection signal outputted from the second optical receiver. This makes it possible to perform the highly accurate noise removal.

A fourth bio-optical measuring apparatus according to an embodiment of the present disclosure includes a light source that emits coherent light; and two or more optical receivers that receive reflected light from a living body, of the light outputted from the light source toward the living body. The fourth bio-optical measuring apparatus further includes a signal processing unit that obtains a low-noise signal by performing averaging processing based on detection signals outputted from the respective optical receivers in response to reception of the reflected light and a statistical signal obtained by performing statistical processing using the respective detection signals.

In the fourth bio-optical measuring apparatus according to the embodiment of the present disclosure is performed the averaging processing based on the detection signals outputted from the respective optical receivers in response to the reception of the reflected light and the statistical signal obtained by performing the statistical processing using the respective detection signals. This makes it possible to perform the highly accurate noise removal.

According to the first bio-optical measuring apparatus according to the embodiment of the present disclosure, the low-noise signal is obtained by performing the averaging processing based on the detection signal outputted from each of the optical receivers in response to the reception of the reflected light, thus making it possible to perform the highly accurate noise removal with a small number of devices.

According to the second bio-optical measuring apparatus according to the embodiment of the present disclosure, the low-noise signal is obtained by performing the averaging processing based on the first detection signal outputted from each of the first optical receivers in response to the reception of the first reflected light and the second detection signal outputted from the second optical receiver in response to the reception of the second reflected light, thus making it possible to perform the highly accurate noise removal with the small number of devices.

According to the third bio-optical measuring apparatus according to the embodiment of the present disclosure, the low-noise signal is obtained by performing the averaging processing based on the first detection signal outputted from each of the first optical receivers in response to the reception of the reflected light and the second detection signal outputted from the second optical receiver, thus making it possible to perform the highly accurate noise removal with the small number of devices.

According to the fourth bio-optical measuring apparatus according to the embodiment of the present disclosure, the low-noise signal is obtained by performing the averaging processing based on the detection signals outputted from the respective optical receivers in response to the reception of the reflected light and the statistical signal obtained by performing the statistical processing using the respective detection signals, thus making it possible to perform the highly accurate noise removal with the small number of devices.

It is to be noted that effects of the present disclosure are not necessarily limited to the effects described here, and any effect described herein may be provided.

BRIEF DESCRIPTION OF DRAWINGS

FIG. 1 is a diagram illustrating an example of a schematic configuration of a bio-optical measuring apparatus according to a first embodiment of the present disclosure.

FIG. 2 is a diagram illustrating an example of a plane configuration of an optical module of FIG. 1.

FIG. 3 is a diagram illustrating an example of a beat signal obtained by an optical receiver of FIG. 1.

FIG. 4 is a diagram illustrating an example of a power spectrum obtained from the beat signal of FIG. 3.

FIG. 5 is a diagram illustrating an example of the averaged power spectrum.

FIG. 6 is a diagram illustrating an example of a relation between the number of channels and noise variations.

FIG. 7 is a diagram illustrating an example of a schematic configuration of a bio-optical measuring apparatus according to a second embodiment of the present disclosure.

FIG. 8 is a diagram illustrating an example of a plane configuration of an optical module of FIG. 7.

FIG. 9 is a diagram illustrating an example of a plane configuration of the optical module of FIG. 7.

FIG. 10 is a diagram illustrating a modification example of a schematic configuration of the bio-optical measuring apparatus of FIG. 1.

FIG. 11 is a diagram illustrating a modification example of a schematic configuration of the bio-optical measuring apparatus of FIG. 7.

FIG. 12 is a diagram illustrating a modification example of the schematic configuration of the bio-optical measuring apparatus of FIG. 1.

FIG. 13 is a diagram illustrating a modification example of the schematic configuration of the bio-optical measuring apparatus of FIG. 7.

FIG. 14 is a diagram illustrating a modification example of the schematic configuration of the bio-optical measuring apparatus of FIG. 1.

FIG. 15 is a diagram illustrating an example of a schematic configuration of a bio-optical measuring apparatus according to a third embodiment of the present disclosure.

FIG. 16 is a diagram illustrating an example of raw waveforms of detection signals of respective optical receiving devices.

FIG. 17 is a diagram illustrating an example of a waveform of a principal component obtained by performing a principal component analysis using the two detection signals of FIG. 16.

FIG. 18 is a diagram illustrating an example of waveforms obtained by removing the principal component of FIG. 17 from the respective detection signals of FIG. 16.

FIG. 19 is a diagram illustrating a modification example of a coupling mode of the optical receiver and a differential circuit in the first embodiment.

FIG. 20 is a diagram illustrating a modification example of a coupling mode of a correction unit and a differential unit in the first embodiment.

FIG. 21 is a diagram illustrating an example of a schematic configuration of a bio-optical measuring apparatus according to a fourth embodiment of the present disclosure.

FIG. 22 is a diagram illustrating an example of a plane configuration of an optical module of FIG. 21.

FIG. 23 is a diagram explaining about a measurement principle in the bio-optical measuring apparatus of FIG. 21.

FIG. 24 is a diagram illustrating an example of a relation between a stage speed and a speed index obtained from an optical receiver when a particle is included in a sample and when no particle is included in the sample.

FIG. 25 is a diagram illustrating an example of a change with time in the speed index when a distance from a light source to an optical receiver is long.

FIG. 26 is a diagram illustrating an example of the change with time in the speed index when the distance from the light source to the optical receiver is short.

FIG. 27 is a diagram illustrating a modification example of a schematic configuration of the bio-optical measuring apparatus of FIG. 21.

FIG. 28 is a diagram illustrating a modification example of the schematic configuration of the bio-optical measuring apparatus of FIG. 21.

FIG. 29 is a diagram illustrating a modification example of the schematic configuration of the bio-optical measuring apparatus of FIG. 21.

FIG. 30 is a diagram illustrating a modification example of the schematic configuration of the bio-optical measuring apparatus of FIG. 21.

FIG. 31 is a diagram illustrating an example of a plane configuration of an optical module provided in the bio-optical measuring apparatus of FIG. 30.

FIG. 32 is a diagram illustrating a modification example of the plane configuration of the optical module provided in the bio-optical measuring apparatus of FIG. 30.

FIG. 33 is a diagram illustrating an example of a change with time in the speed index when the distance from the light source to the optical receiver is long.

FIG. 34 is a diagram illustrating an example of a change with time in a standard deviation of a detection signal when the distance from the light source to the optical receiver is short.

FIG. 35 is a diagram illustrating an example of a relation between the standard deviation of FIG. 34 and the speed index of FIG. 33.

FIG. 36 is a diagram illustrating an example of the change with time in the speed index of FIG. 33, from which motion noise has been removed, by using a mathematical function having the standard deviation of FIG. 34 as a parameter and in the speed index of FIG. 33.

MODES FOR CARRYING OUT THE INVENTION

In the following, description is given in detail of some embodiments for carrying out the present disclosure, with reference to the drawings. It is to be noted that description is given in the following order.
1. First Embodiment
2. Second Embodiment
3. Modification Examples of First or Second Embodiment
4. Third Embodiment
5. Fourth Embodiment
6. Modification Examples of Fourth Embodiment

1. First Embodiment

[Configuration]

Description is given of a bio-optical measuring apparatus 1 according to a first embodiment of the present disclosure. FIG. 1 is a diagram illustrating an example of a schematic configuration of the bio-optical measuring apparatus 1. The bio-optical measuring apparatus 1 is an apparatus that detects a blood flow rate, which is biological information of a living body 100. The bio-optical measuring apparatus 1 includes, for example, an optical module 10, a plurality of differential circuits 20, a plurality of ADCs (Analog-Digital Converters) 30, and a signal processing unit 40. As illustrated in FIG. 2, for example, the optical module 10 includes one light source 11 and three or more optical receivers 12 on a substrate 10A. The substrate 10A is, for example, a wiring board that electrically and mutually couples the optical receivers 12 to the differential circuits 20. The substrate 10A is also a support substrate that supports the one light source 11 and the three or more optical receivers 12.

The substrate 10A has a wiring layer formed on, for example, a resin substrate, a resin film, or a glass substrate. The light source 11 includes, for example, a semiconductor light source, such as an LD (Laser Diode: semiconductor laser), which emits coherent light. The light source 11 emits light La having a luminescence wavelength in a visible region, a near-infrared region, or an infrared region. The light source 11 emits the light La having a component in a normal direction of the substrate 10A. As a result of this, the light source 11 emits the light La toward the living body 100 when the bio-optical measuring apparatus 1 is attached to the living body 100. Each of the optical receivers 12 includes, for example, a PD (Photo Diode: photodiode). It is preferable that each of the optical receivers 12 be configured so as to output a mutually equal detection signal when light having a mutually equal amplitude and frequency is inputted. It is preferable that, for example, each of the optical receivers 12 be configured with mutually equal materials, and in a mutually equal structure and size.

The one light source 11 and the three or more optical receivers 12 are disposed (mounted) on one surface of the substrate 10A, for example. Each of the optical receivers 12 is disposed at a position a predetermined distance away from the light source 11. It is preferable that the respective optical receivers 12 be disposed at the positions each having a distance from the light source 11 which is substantially equal to each other. At this time, the plurality of optical receivers 12 is disposed annularly so as to surround a circumference of the light source 11, for example. When the optical module 10 is attached to the living body 100, it is preferable that a mechanism be provided in the bio-optical measuring apparatus 1 that closely adheres, to the living body 100, a surface of the optical module 10, on which the light source 11 and the three or more optical receivers 12 are mounted.

The respective optical receivers 12 receive reflected light Lb from the living body 100, of light outputted from the light source 11 toward the living body 100. That is, the respective optical receivers 12 are disposed at positions where the reflected light Lb from the living body 100 is receivable, of the light outputted from the light source 11 toward the living body 100. The reflected light Lb corresponds to the light that is outputted from the light source 11 and back scattered by the living body 100. When the reflected light Lb from the living body 100 is inputted, the respective optical receivers 12 output detection signals corresponding to the inputted reflected light Lb.

The differential circuits 20 are each electrically coupled to corresponding output end of the two optical receivers 12 of the plurality of optical receivers 12. Here, in each of the differential circuits 20, the one optical receiver 12 of the two electrically coupled optical receivers 12 is the optical receiver 12 that is common to each other. That is, the output end of the one optical receiver 12 is electrically coupled to an input end of all of the differential circuits 20. In contrast, in each of the differential circuits 20, the other optical receiver 12 of the two electrically coupled optical receivers 12 is the optical receiver 12 that is different from each other. In the following, the one optical receiver 12 coupled to the input ends of all of the differential circuits 20 is referred to as an optical receiver 12A. In addition, in the following, each of the optical receivers 12 excluding the optical receiver 12A of the plurality of optical receivers 12 is referred to as an optical receiver 12B.

When the reflected light Lb from the living body 100 is inputted, the optical receiver 12A outputs a detection signal 12a corresponding to the inputted reflected light Lb. When the reflected light Lb from the living body 100 is inputted, the respective optical receivers 12B output detection signals 12b corresponding to the inputted reflected light Lb. Here, the optical receiver 12A and the respective optical receivers 12B are each disposed at the position having the substantially equal distance from the light source 11, and thus in-phase noise included in the detection signal 12a and the respective detection signals 12b is substantially equal.

On the basis of the plurality of detection signals (12a, 12b) outputted from the plurality of optical receivers 12 in response to reception of the reflected light Lb, the plurality of differential circuits 20 generates differential signals 20a in which the in-phase noise has been reduced and the number of which is larger than half of the number of the optical receivers 12. For example, on the basis of the plurality of detection signals (12a, 12b) outputted from the plurality of optical receivers 12 in response to the reception of the reflected light Lb, the plurality of differential circuits 20 generates the differential signals 20a in which the in-phase noise has been reduced and the number of which is one smaller than the number of the optical receivers 12. The differential signals 20a each correspond to a specific example of a "first correction signal" of the present disclosure. The plurality of differential circuits 20 obtains the respective differential signals 20a by, for example, making the detection signal 12a outputted from the one optical receiver 12A of the three or more optical receivers 12 a reference signal and deriving differences between the reference signal and the respective detection signals 12b excluding the reference signal of the detection signals (12a, 12b) outputted from the respective optical receivers 12.

The respective differential circuits 20, for example, derive the differences between the detection signal 12a, which is the reference signal, inputted from the optical receiver 12A and the detection signals 12b inputted from the optical receivers 12B and thereby obtain the differential signals 20a. The differential circuits 20 output, to the ADCs 30, the differential signals 20a thus obtained. The differential signals 20a at this time are each a beat signal as illustrated in FIG. 3, for example. The beat signal is generated by a frequency shift caused by blood flow in the living body 100, for example. The frequency shift is caused by a laser Doppler effect. The ADCs 30 each convert the differential signals 20a inputted from the differential circuits 20 from an analog signal to a digital signal and output digital differential signals 20a to the signal processing unit 40.

The signal processing unit 40 performs control of light emission of the light source 11 or control of light reception of the respective optical receivers 12. The signal processing unit 40 further derives the blood flow rate by processing signals inputted from the respective differential circuits 20. The signal processing unit 40 obtains a low-noise signal 40a by performing averaging processing using the plurality of differential signals 20a that is obtained as a result of the plurality of differential circuits 20 reducing the in-phase noise. Specifically, the signal processing unit 40 derives a power spectrum as illustrated in FIG. 4, for example, for each of the differential signals 20a, by performing FFT (Fast Fourier Transform) on the plurality of digital differential signals 20a inputted from the plurality of ADCs 30. The power spectrum of FIG. 4 has a waveform with much noise. The signal processing unit 40 further derives an averaged power spectrum as illustrated in FIG. 5, for example, by performing the averaging processing using a plurality of derived power spectra. Here, the averaging processing refers to, for example, mutually adding the plurality of power spectra derived from the plurality of differential signals 20a and dividing it by the number of additions of the power spectra. The power spectrum of FIG. 5 has a wavelength with less noise, as compared to the power spectrum of FIG. 4. In a case where the number of optical receivers 12B (number of channels) is 7, noise variations are extremely small, as illustrated in FIG. 6, for example. Note that it is seen from FIG. 6 that the noise variations decrease by 1/√ (number of channels) as the number of the channels increases. One reason for this is that performing differential amplification with the differential circuits 20 reduces the in-phase noise among the respective channels and signals of the respective channels are signals independent of each other.

The signal processing unit 40 derives the blood flow rate, which is the biological information of the living body 100, on the basis of the obtained low-noise signal 40a. A signal processing circuit 40 derives the blood flow rate by, for example, performing an integration on the obtained low-noise signal 40a in an appropriate frequency range and deriving a primary moment.

[Effects]

In the following, description is given of effects of the bio-optical measuring apparatus 1.

There has been a technology called a laser Doppler blood-flowmeter that noninvasively measures the blood flow rate under the skin by irradiating the human skin with the coherent light and analyzing backscattered light thereof. The technology has already been commercially available as a measuring instrument. In such a measuring instrument, signal perturbation is caused by various types of noise, which thus leads to a demand for the highly accurate noise removal. In addition, reduction of the number of devices used for the noise removal is requested. In an existing method, however, the noise removal has been performed by derivation of differential signals for each pair of independent optical receivers, which thus makes a large number of devices necessary for the highly accurate noise removal.

In contrast, in the present embodiment, the differential signals 20a are generated in which the in-phase noise has been reduced and the number of which is larger than the half of the number of the optical receivers 12 (for example, the number being one smaller than the number of the optical receivers 12), on the basis of the detection signals 12a and 12b outputted from the respective optical receivers 12 in response to the reception of the reflected light Lb. Then, the low-noise signal 40a is obtained by performing the averaging processing using the plurality of generated differential signals 20a. This makes it possible to reduce the number of devices than in a case where the noise removal is performed by the derivation of the differential signals for each pair of the independent optical receivers, and further to perform the highly accurate noise removal. Therefore, it is possible to perform the highly accurate noise removal with the small number of devices.

In addition, in the present embodiment, the detection signal 12a outputted from the one optical receiver 12A of the three or more optical receivers 12 is made the reference signal. By deriving the differences between this reference signal and the respective detection signals 12b, excluding the reference signal, of the plurality of detection signals (12a, 12b) outputted from the plurality of optical receivers 12, it is possible to obtain the plurality of differential signals 20a the number of which is same as the number of the optical receivers 12B (number of channels). This makes it possible to reduce the number of devices than in the case where the noise removal is performed by the derivation of the differential signals for each pair of the independent optical receivers, and further to perform the highly accurate noise removal. Therefore, it is possible to perform the highly accurate noise removal with the small number of devices.

In addition, in the present embodiment, in a case where each of the optical receivers 12 is disposed at the position having the distance from the light source 11 which is substantially equal to each other, it is possible to remove the in-phase noise from the respective detection signals 12b with the very high accuracy. Therefore, it is possible to perform the highly accurate noise removal with the small number of devices.

Moreover, in the present embodiment, the blood flow rate, which is the biological information of the living body 100, is calculated on the basis of the beat signal (differential signal 20a) that is included in the low-noise signal 40a and generated by a laser Doppler. In this manner, use of the low-noise signal 40a in calculation of the blood flow rate, which is the biological information of the living body 100, makes it possible to perform the highly accurate noise removal with the small number of devices.

2. Second Embodiment

[Configuration]

In the following, description is given of a bio-optical measuring apparatus 2 according to a second embodiment of the present disclosure. FIG. 7 is a diagram illustrating an example of a plane configuration of the bio-optical measuring apparatus 2 of the present embodiment.

The bio-optical measuring apparatus 2 is an apparatus that detects the blood flow rate, which is the biological information of the living body 100. The bio-optical measuring apparatus 2 includes an optical module 50 in place of the optical module 10 in the bio-optical measuring apparatus 1 of the aforementioned embodiment.

FIG. 8 and FIG. 9 illustrate an example of a plane configuration of the optical module 50. The optical module 50 includes, for example, one light source 11 and three or more optical receivers 12 on a substrate 50A. The substrate 50A has a similar configuration to the configuration of the substrate 10A. The one light source 11 and the three or more optical receivers 12 are disposed (mounted) on one surface of the substrate 50A. Each of the optical receivers 12 is disposed at a position a predetermined distance away from the light-emitting device 11. The respective optical receivers 12 are disposed in matrix at positions adjacent to the light source 11. The optical receiver 12A is, for example, the optical receiver 12 located at a middle of the plurality of optical receivers 12 disposed in the matrix. It is to be noted that the position of the optical receiver 12A is not limited to the position illustrated in FIG. 8. It is to be noted that the respective optical receivers 12 may include some optical receiving sections in an image sensor 50B, as illustrated in FIG. 9, for example. The image sensor 50B is, for example, a CCD (charge Coupled Device) image sensor or a CMOS (Complementary Metal-Oxide Semiconductor) image sensor.

The bio-optical measuring apparatus 2 includes one each of the ADCs 30 for each of the optical receivers 12. In the bio-optical measuring apparatus 2, the ADCs 30 are each electrically coupled to corresponding output end of the optical receivers 12. The bio-optical measuring apparatus 2 further includes one each of correction units 61 for each of the ADCs 30. In the bio-optical measuring apparatus 2, the correction units 61 are each electrically coupled to corresponding output end of the ADCs 30.

The bio-optical measuring apparatus 2 includes a plurality of differential units 62. Output of the two correction units 61 of the plurality of correction units 61 is inputted to each of the differential units 62. Here, in each of the differential units 62, the one correction unit 61 (60A) of the two correction units 61 whose output is received is the correction unit 61 common to each other. That is, the output of the one correction unit 61 is inputted to all of the differential units 62. In contrast, in the respective differential units 62, the other correction unit 61 (60B) of the two correction units 61 whose output is received is the correction unit 61 that is different from each other. In the following, the one correction unit 61 that performs input to all of the differential units 62 is referred to as a correction unit 61A. In addition, in the following, each of the correction units 61, excluding the correction unit 61A, of the plurality of correction units 61 is referred to as a correction unit 61B.

The ADC 30 coupled to the output end of the optical receiver 12A converts the detection signal 12a inputted from the optical receiver 12A from the analog signal to the digital signal and outputs the digital detection signal 12a to the correction unit 61A. The respective ADCs 30 coupled to the output ends of the optical receivers 12B convert the detection signals 12b inputted from the optical receivers 12B from the analog signal to the digital signal and output the digital detection signals 12b to the correction units 61B.

The correction unit 61A performs, on the detection signal 12a, correction corresponding to a distance of the corresponding optical receiver 12A from the light source 11 and thereby obtains a correction signal 61a (second correction signal). That is, the correction signal 61a is a signal corresponding to the detection signal 12a outputted from the optical receiver 12A in response to the reception of the reflected light Lb. The correction unit 61A obtains the correction signal 61a by, for example, multiplying the detection signal 12a by a correction coefficient that corresponds to the distance of the corresponding optical receiver 12 from the light source 11. The correction unit 61A outputs the obtained correction signal 61a to each of the differential units 62.

The correction units 61B perform, on the detection signals 12b, the correction corresponding to the distance of the corresponding optical receivers 12B from the light source 11 and thereby obtain correction signals 61b (second correction signals). That is, the correction signals 61b are signals corresponding to the detection signals 12b outputted from the respective optical receivers 12B in response to the reception of the reflected light Lb. In addition, the correction signals 61b are signals that correspond to the respective detection signals 12b obtained from the plurality of optical receivers 12B, excluding at least one optical receiver 12A of the three or more optical receivers 12. The correction units 61B obtain the correction signals 61b by, for example, multiplying the detection signals 12b by the correction coefficient, which corresponds to the distance of the corresponding optical receiver 12 from the light source 11. The correction units 61B output the obtained correction signals 61b to the differential units 62.

On the basis of the plurality of correction signals (61a, 61b), the plurality of differential units 62 generates the differential signals 20a in which the in-phase noise has been reduced and the number of which is larger than the half of the number of the optical receivers 12 (for example, the number being one smaller than the number of the optical receivers 12). The plurality of differential units 62 obtains the respective differential signals 20a by, for example, making the correction signal 61a the reference signal and deriving a difference between that reference signal and each of the correction signals 61b.

The respective differential units 62 derive differences between the correction signal 61a and the correction signals 61b, for example, and thereby obtain the differential signals 20a. The correction signal 61a is inputted from the correction unit 61A and corresponds to the detection signal 12a that is the reference signal. The correction signals 61b are inputted from the correction units 61B and correspond to the detection signals 12b. The respective differential units 62 output, to the signal processing unit 40, the differential signals 20a which have been thus obtained. The differential signals 20a at this time are digital beat signals.

The signal processing unit 40 obtains the low-noise signal 40a by performing the averaging processing using the plurality of differential signals 20a in which the in-phase noise has been reduced by the plurality of differential units 62. Specifically, the signal processing unit 40 derives, for example, the power spectrum as illustrated in FIG. 4 for each of the differential signals 20a by performing the FFT on the plurality of digital differential signals 20a inputted from the plurality of differential units 62. The signal processing circuit 40 further derives, for example, the averaged power spectrum as illustrated in FIG. 5 by performing the averaging processing using the plurality of derived power spectra. The power spectrum of FIG. 5 has the waveform with less noise than the power spectrum of FIG. 4.

The signal processing unit 40 derives the blood flow rate, which is the biological information of the living body 100, on the basis of the obtained low-noise signal 40a. The signal processing circuit 40 derives the blood flow rate by, for example, performing the integration on the obtained low-noise signal 40a in the appropriate frequency range and deriving the primary moment.

[Effects]

In the following, description is given of the effects of the bio-optical measuring apparatus 2.

In the present embodiment, the differential signals 20a are generated in which the in-phase noise has been reduced and the number of which is larger than the half of the number of the optical receivers 12 (for example, the number being one smaller than the number of the optical receivers 12), on the basis of the correction signals 61a and 61b that correspond to the detection signals 12a and 12b outputted from the respective optical receivers 12 in response to the reception of the reflected light Lb. Then, the low-noise signal 40a is obtained by performing the averaging processing using the plurality of generated differential signals 20a. This makes it possible to reduce the number of devices than in the case where the noise removal is performed by the derivation of the differential signals for each pair of the independent optical receivers, and further to perform the highly accurate noise removal. Therefore, it is possible to perform the highly accurate noise removal with the small number of devices.

In addition, in the present embodiment, the respective differential signals 20a are obtained on the basis of the respective correction signals (61a, 61b). The respective correction signals (61a, 61b) are obtained by the correction being performed on the respective detection signals (12a, 12b). The correction corresponds to the distance from the light source 11 of the optical receivers 12 from which the detection signals (12a, 12b) are obtained.

In addition, in the present embodiment, the correction signal 61a outputted from the one correction unit 61A of the three or more correction units 61 is made the reference signal. By deriving the differences between this reference signal and the respective correction signals 61b, excluding the reference signal, of the plurality of correction signals (61a, 61b) outputted from the plurality of correction units 61, it is possible to obtain the plurality of differential signals 20a the number of which is same as the number of the optical receivers 12B (number of channels). This makes it possible to reduce the number of devices than in the case where the noise removal is performed by the derivation of the differential signals for each pair of the independent optical receivers, and further to perform the highly accurate noise removal. Therefore, it is possible to perform the highly accurate noise removal with the small number of devices.

In addition, in the present embodiment, in a case where the plurality of optical receivers 12 includes one image sensor 10B, variations in each of the optical receivers 12 is extremely small. This makes it possible to perform the highly accurate noise removal with the small number of devices.

Moreover, in the present embodiment, the blood flow rate, which is the biological information of the living body 100, is calculated on the basis of the beat signal (differential signal 20a) that is included in the low-noise signal 40a and generated by a laser Doppler. In this manner, use of the low-noise signal 40a in calculation of the blood flow rate, which is the biological information of the living body 100, makes it possible to perform the highly accurate noise removal with the small number of devices.

3. Modification Examples of First or Second Embodiment

In the following, description is given of modification examples of the bio-optical measuring apparatus 1 according to the aforementioned first embodiment or modification examples of the bio-optical measuring apparatus 2 according to the aforementioned second embodiment.

[Modification Example A]

FIG. 10 illustrates a modification example of a schematic configuration of the bio-optical measuring apparatus 1. A bio-optical measuring apparatus 1 according to this modification example is the bio-optical measuring apparatus 1 of the aforementioned first embodiment in which a reflective plate 13 that reflects the light outputted from the light source 11 is further provided. The reflective plate 13 may be a total reflection mirror or a half mirror, for example. The reflective plate 13 is disposed at a position where some of the light outputted from the light source 11 enters the optical receiver 12A due to reflection by the reflective plate 13. It is preferable that at this time, the optical module 10 be configured so as to prevent the reflected light Lb from entering the optical receiver 12A.

In this modification example, the optical receiver 12A (second optical receiver) receives reflected light Lc (second reflected light) reflected by the reflective plate 13, of the light outputted from the light source 11. In contrast, the respective optical receivers 12B (first optical receivers) receive the reflected light Lb (first reflected light) from the living body 100, of the light La outputted from the light source 11 toward the living body 100. Furthermore, in this modification example, on the basis of the detection signals 12b (first detection signals) outputted from the plurality of optical receivers 12B in response to the reception of the reflected light Lb and the detection signal 12a (second detection signal) outputted from the optical receiver 12A in response to reception of the reflected light Lc, the plurality of differential circuits 20 generates the differential signals 20a (first correction signals) in which the in-phase noise has been reduced and the number of which is larger than the half of the number of optical receivers 12 (specifically, the number being one smaller than the number of the optical receivers 12). The signal processing unit 40 obtains the low-noise signal 40a by performing the averaging processing using the plurality of generated differential signals 20a. The signal processing unit 40 calculates the blood flow rate on the basis of the beat signal that is included in the low-noise signal 40a and generated by the laser Doppler.

In this modification example, the detection signal 12a outputted from the optical receiver 12A includes no or little noise caused by the living body 100. This makes it possible to effectively remove the in-phase noise (that is, common mode noise) caused by intensity modulation or a power source of the light source 11, by deriving a difference between the detection signal 12a and each of the detection signals 12b. Therefore, it is possible to perform the highly accurate noise removal with the small number of devices. Moreover, calculation of the blood flow rate on the basis of the low-noise signal 40a in which the in-phase noise has been thus reduced makes it possible to derive the highly accurate blood flow rate.

[Modification Example B]

FIG. 11 illustrates a modification example of a schematic configuration of the bio-optical measuring apparatus 2. A bio-optical measuring apparatus 2 according to this modification example is the bio-optical measuring apparatus 2 of the aforementioned second embodiment in which the reflective plate 13 that reflects the light outputted from the light source 11 is further provided. The reflective plate 13 may be the total reflection mirror or the half mirror, for example. The reflective plate 13 is disposed at the position where some of the light outputted from the light source 11 enters the optical receiver 12A due to the reflection by the reflective plate 13. It is preferable that at this time, the optical module 50 be configured so as to prevent the reflected light Lb from entering the optical receiver 12A.

In this modification example, the optical receiver 12A (second optical receiver) receives the reflected light Lc (second reflected light) reflected by the reflective plate 13, of the light outputted from the light source 11. In contrast, the respective optical receivers 12B (first optical receivers) receive the reflected light Lb (first reflected light) from the living body 100, of the light La outputted from the light source 11 toward the living body 100. Furthermore, in this modification example, on the basis of the correction signals 61b corresponding to the respective detection signals 12b (first detection signals) outputted from the plurality of optical receivers 12B in response to the reception of the reflected light Lb and the correction signal 61a corresponding to the detection signal 12a (second detection signal) inputted from the optical receiver 12A in response to the reception of the reflected light Lc, the plurality of differential units 62 generates the differential signals 20a (first correction signals) in which the in-phase noise has been reduced and the number of which is larger than the half of the number of the optical receivers 12 (specifically, the number being one smaller than the number of the optical receivers 12). The signal processing unit 40 obtains the low-noise signal 40a by performing the averaging processing using the plurality of generated differential signals 20a. The signal processing unit 40 calculates the blood flow rate on the basis of the beat signal that is included in the low-noise signal 40a and generated by the laser Doppler.

In this modification example, the detection signal 12a outputted from the optical receiver 12A includes no or little noise caused by the living body 100. This makes it possible to effectively remove the in-phase noise (that is, the common mode noise) caused by the intensity modulation or the power source of the light source 11, by deriving the difference between the detection signal 12a and each of the detection signals 12b. Therefore, it is possible to perform the highly accurate noise removal with the small number of devices. Moreover, the calculation of the blood flow rate on the basis of the low-noise signal 40a from which the in-phase noise has been thus removed makes it possible to derive the highly accurate blood flow rate.

[Modification Example C]

FIG. 12 illustrates a modification example of the schematic configuration of the bio-optical measuring apparatus 1. A bio-optical measuring apparatus 1 according to this modification example corresponds to the bio-optical measuring apparatus 1 according to the aforementioned Modification Example A in which a light-shielding plate 14 that blocks transmission of the light outputted from the light source 11 is provided in place of the reflective plate 13.

In this modification example, no light enters the optical receiver 12A from outside, and thus the detection signal 12a outputted from the optical receiver 12A does not include noise caused by the light source 11. Therefore, in a case where the noise caused by the light source 11 is extremely small, application of this modification example is preferable. In this modification example, because the light outputted from the light source 11 is not blocked by a mirror or the like, it is possible to remove the noise without reducing an amount of light.

[Modification Example D]

FIG. 13 illustrates a modification example of the schematic configuration of the bio-optical measuring apparatus 2. A bio-optical measuring apparatus 2 according to this modification example corresponds to the bio-optical measuring apparatus 2 according to the aforementioned Modification Example B in which the light-shielding plate 14 that blocks the transmission of the light outputted from the light source 11 is provided in place of the reflective plate 13.

In this modification example, no light enters the optical receiver 12A from the outside, and thus the detection signal 12a outputted from the optical receiver 12A does not include the noise due to the light source 11. Therefore, in a case where the noise caused by the light source 11 is extremely small, application of this modification example is preferable. In this modification example, as compared to Modification Example B, there is a difference that the detection signal 12a does not include the noise caused by the light source 11. However, as to any points other than that, the effects similar to those of the bio-optical measuring apparatus 1 according to Modification Example B are obtained.

[Modification Example E]

FIG. 14 illustrates a modification example of the schematic configuration of the bio-optical measuring apparatus 1. A bio-optical measuring apparatus 1 according to this modification example corresponds to the bio-optical measuring apparatus 1 according to the aforementioned first embodiment in which a SW (switch device) 70 that selects one output end from the output ends of the plurality of differential circuits 20 is further provided, and only one ADC 30 is provided in a stage following the SW 70. In this modification example, provision of the SW 70 makes it possible to reduce the number of ADCs 30 to one, which thus allows for reduction of the number of devices corresponding to the reduced number of the ADCs 30. In this modification example, however, due to a switching operation by the SW 70, timing of AD conversion in the ADC 30 differs in each of the differential circuits 20. This improves the noise removal effect in the averaging processing in the signal processing circuit 40.

4. Third Embodiment

[Configuration]

In the following, description is given of a bio-optical measuring apparatus 3 according to a third embodiment of the present disclosure. FIG. 15 illustrates an example of a schematic configuration of the bio-optical measuring apparatus 3 of the present embodiment. The bio-optical measuring apparatus 3 is an apparatus that detects the blood flow rate, which is the biological information of the living body 100. The bio-optical measuring apparatus 3 includes, for example, an optical module 10, a plurality of ADCs 30, a principal component analysis unit 80, a plurality of in-phase noise removal units 90, and a signal processing unit 40.

In the bio-optical measuring apparatus 3, one each of the ADCs 30 is provided for each of optical receivers 12, and each of the ADCs 30 is electrically coupled to the corresponding output end of the optical receivers 12. The ADCs 30 convert detection signals 12c inputted from the optical receivers 12 from the analog signal to the digital signal and output digital detection signals 12c to the principal component analysis unit 80 and the in-phase noise removal units 90. For example, outputs (detection signals 12c) of the ADCs 30 corresponding to the respective optical receivers 12 are inputted to the principal component analysis unit 80. Output of the principal component analysis unit 80 is inputted to each of the in-phase noise removal units 90. In the bio-optical measuring apparatus 3, one each of the in-phase noise removal units 90 is further provided for each of the ADCs 30, and the outputs of the ADCs 30 are inputted to the respective in-phase noise removal units 90. Output of each of the in-phase noise removal units 90 is inputted to the signal processing unit 40.

The principal component analysis unit 80 performs statistical processing on the detection signals 12c obtained in the respective optical receivers 12 (respective channels), for example. The optical receiver 12 of a channel ch0 or the optical receiver 12 of a channel ch1 outputs a signal having a waveform as illustrated in FIG. 16, for example. Here, the statistical processing is, for example, a principal component analysis, singular value decomposition, or an independent component analysis. The principal component analysis unit 80 performs the principal component analysis on the detection signals 12c obtained at the respective optical receivers 12 (respective channels), for example, and extracts a first principal component. The first principal component has a waveform as illustrated in FIG. 17, for example. The principal component analysis unit 80 outputs a statistical signal 80a (for example, the extracted first principal component) obtained by performing the statistical processing to each of the in-phase noise removal units 90.

The respective in-phase noise removal units 90 generate differential signals 90a in which the in-phase noise has been reduced and the number of which is larger than the half of the number of the optical receivers 12 (specifically, the number being same as the number of the optical receivers 12), on the basis of the detection signals 12c inputted from the corresponding ADCs 30 and the statistical signal 80a inputted from the principal component analysis unit 80. The differential signals 90a each correspond to a specific example of the "correction signal" of the present disclosure. The differential signal 90a is the beat signal as illustrated in FIG. 18, for example. The respective in-phase noise removal units 90 obtain the differential signals 90a by, for example, taking differences between the detection signals 12c inputted from the corresponding ADCs 30 and the statistical signal 80a inputted from the principal component analysis unit 80. The signal processing unit 40 obtains the low-noise signal 40a by performing the averaging processing using the differential signals 90a inputted from the in-phase noise removal units 90. Specifically, the signal processing unit 40 derives the power spectrum as illustrated in FIG. 4, for example, for each of the differential signals 90a by performing the FFT on the plurality of differential signals 90a. The signal processing unit 40 further derives the averaged power spectrum as illustrated in FIG. 5, for example, by performing the averaging processing using the plurality of derived power spectra.

The signal processing unit 40 derives the blood flow rate, which is the biological information of the living body 100, on the basis of the obtained low-noise signal 40a. The signal processing unit 40 derives the blood flow rate by, for example, performing the integration on the obtained low-noise signal 40a in the appropriate frequency range and deriving the primary moment.

[Effects]

In the following, description is given of the effects of the bio-optical measuring apparatus 3.

In the present embodiment, the differential signals 90a are generated in which the in-phase noise has been reduced and the number of which is larger than the half of the number of the optical receivers 12 (specifically, the number being same as the number of the optical receivers 12), on the basis of the detection signals 12c outputted from the respective optical receivers 12 in response to the reception of the reflected light Lb and the statistical signal 80a obtained by performing the statistical processing using each of the detection signals 12c. Then, the low-noise signal 40a is obtained by performing the averaging processing using the plurality of differential signals 90a that have been thereby obtained. This makes it possible to reduce the number of devices than in the case where the noise removal is performed by the derivation of the differential signals for each pair of the independent optical receivers, and further to perform the highly accurate noise removal. Therefore, it is possible to perform the highly accurate noise removal with the small number of devices. Moreover, in the present embodiment, use of the statistical processing makes it possible to apply, to the averaging processing, the differential signals 90a corresponding to the detection signals 12c obtained in all of the optical receivers 12 (channels). Therefore, it is possible to reduce even more noise.

In addition, in the present embodiment, in a case where the statistical processing is the principal component analysis, the singular value decomposition, or the independent component analysis, it is possible to perform the highly accurate noise removal. Therefore, it is possible to perform the highly accurate noise removal with the small number of devices.

In addition, in the present embodiment, the blood flow rate, which is the biological information of the living body 100, is calculated on the basis of the beat signal (differential signal 90a) that is included in the low-noise signal 40a and generated by the laser Doppler. In this manner, the use of the low-noise signal 40a in the calculation of the blood flow rate, which is the biological information of the living body 100, makes it possible to perform the highly accurate noise removal with the small number of devices.

As described above, although description has been given of the present disclosure by presenting a plurality of the embodiments and the modification examples thereof, the present disclosure is not limited to the aforementioned embodiments, or the like, and various modifications are possible.

For example, in the aforementioned first embodiment, the output end of the one optical receiver 12 is electrically coupled to the input ends of all of the differential circuits 20. In the aforementioned first embodiment, however, the input ends of the respective differential circuits 20 may be coupled to any two of the optical receivers 12, as illustrated in FIG. 19, for example. That is, the reference signal inputted to the respective differential circuits 20 need not be a common signal. It is to be noted that FIG. 19 exemplifies a case where the differential circuit 20 is provided for each combination of the two optical receivers 12 that may be selected from the plurality of optical receivers 12.

In addition, in the aforementioned second embodiment, for example, output of the one optical receiver 12 is inputted to all of the differential units 62 via the ADCs 30 and the correction units 61. In the aforementioned second embodiment, however, the input end of each of the differential units 62 may be coupled to any two optical receivers 12 via the ADC 30 and the correction unit 61, as illustrated in FIG. 20, for example. That is, the reference signal inputted to each of the differential units 62 need not be the common signal. It is to be noted that FIG. 20 exemplifies a case where the differential unit 62 is provided for each combination of the two correction units 61 (optical receivers 12) that may be selected from the plurality of correction units 61 (optical receivers 12).

A Doppler blood-flowmeter performs measurements using a light interference phenomenon as described above, and is strongly influenced by a change in an optical path due to motion of a body, or the like. Consequently, in many cases, an existing Doppler blood-flowmeter is used during rest, and there are few cases where it is used in the measurements in everyday life.

There have been few examples in which occurrence of noise due to the motion of the body (motion noise) is suppressed. For example, Japanese Unexamined Patent Application Publication No. H07-092184 and U.S. Pat. No. 6,173,197 disclose technologies that utilize a difference between a frequency of motion noise and a frequency due to Doppler to remove the superimposed motion noise from a frequency distribution of Doppler signals. In these technologies, signal processing is performed, on the assumption that the motion noise is superimposed on a blood flow signal by Doppler. However, the optical path of light changes in a case where the human body actually moves, and thus the blood flow signal itself changes. Therefore, simple use of these technologies is not possible.

In addition, for example, Japanese Unexamined Patent Application Publication No. S63-097146 discloses a technology that detects a contact pressure of a probe and performs measurements when the contact pressure is constant. However, it is natural to think that a human being moves at all times in actual everyday life, and it is believed that a change in the pressure also occurs constantly. Therefore, this technology is not suited to measurements in the everyday life. Then, the inventors of the present application have devised a bio-optical measuring apparatus that suppresses noise due to motions in the everyday life and allows for measurement of the blood flow rate in a stable manner. In the following, description is given of an embodiment of the bio-optical measuring apparatus.

5. Fourth Embodiment

[Configuration]

In the following, description is given of a bio-optical measuring apparatus 4 according to a fourth embodiment of the present disclosure.

FIG. 21 illustrates an example of a schematic configuration of the bio-optical measuring apparatus 4 according to the present embodiment. The bio-optical measuring apparatus 4 is an apparatus that detects the blood flow rate, which is the biological information of the living body 100. The bio-optical measuring apparatus 4 includes, for example, an optical module 110, a plurality of ADCs 120, and a signal processing unit 130. As illustrated in FIG. 22, for example, the optical module 110 includes one light source 11 and two optical receivers 12 on a substrate 110A. The substrate 110A is, for example, a wiring board that electrically and mutually couples the respective optical receivers 12 to the corresponding ADCs 120. The substrate 110A is also a support substrate that supports the one light source 11 and the two optical receivers 12.

The substrate 110A has the wiring layer formed on, for example, the resin substrate, the resin film, or the glass substrate. The light source 11 emits light La having the component in the normal direction of the substrate 110A. With this, the light source 11 emits the light La toward the living body 100 when the bio-optical measuring apparatus 4 is attached to the living body 100.

The one light source 11 and the two optical receivers 12 are disposed (mounted) on one surface of the substrate 110A, for example. The two optical receivers 12 are disposed at two positions on the substrate 110A, each having a mutually different distance from the light source 11 in a predetermined direction from the light source 11. In the following, of the two optical receivers 12, the optical receiver that is relatively close to the light source 11 is referred to as an optical receiver 12C and the optical receiver that is relatively far from the light source 11 is referred to as an optical receiver 12D.

The "predetermined direction" is a concept including rough bearings such as right side to the light source 11, left side to the light source 11, upper side to the light source 11, or the lower side to the light source 11 when an observer views the light source 11 from the normal direction of the substrate 110A, for example. Therefore, the two optical receivers 12 may be disposed on a straight line, for example, or may be disposed at positions off the straight line in a range recognizable as a predetermined bearing from the light source 11.

The respective optical receivers 12 receive reflected light Lb from the living body 100, of the light outputted from the light source 11 toward the living body 100. That is, the respective optical receivers 12 are disposed at positions where the reflected light Lb from the living body 100 is receivable, of the light outputted from the light source 11 toward the living body 100. The reflected light Lb corresponds to the light that is outputted from the light source 11 and back scattered by the living body 100. When the reflected light Lb from the living body 100 is inputted, the respective optical receivers 12 output detection signals corresponding to the inputted reflected light Lb. When reflected light Lb (Lb1) from the living body 100 is inputted, the optical receiver 12C outputs a detection signal $12c1$ corresponding to the inputted reflected light Lb (Lb1). When reflected light Lb (Lb2) from the living body 100 is inputted, the optical receiver 12D outputs a detection signal $12d1$ corresponding to the inputted reflected light Lb (Lb2).

The ADCs 120 convert detection signals inputted from the optical receivers 12 from the analog signal to the digital signal and output the detection signals as digital detection signals $120a$ to the signal processing unit 130. When the detection signal is inputted from the optical receiver 12C, the corresponding ADC 120 coupled to the optical receiver 12C outputs a digital detection signal $120a$ ($120a1$). When the detection signal is inputted from the optical receiver 12D, the corresponding ADC 120 coupled to the optical receiver 12D outputs a digital detection signal $120a$ ($120a2$).

The signal processing unit 130 performs the control of light emission of the light source 11 or the control of light reception of the respective optical receivers 12. The signal processing unit 130 further derives the blood flow rate by processing the detection signals $120a$ inputted from the respective ADCs 120. The signal processing unit 130 obtains the low-noise signal, on the basis of the detection signals $120a$ obtained at the two ADCs 120. The signal processing unit 130 derives the blood flow rate, which is the biological information of the living body 100, on the basis of the obtained low-noise signal. A signal processing circuit 130 derives the blood flow rate by, for example, performing the integration on the obtained low-noise signal in the appropriate frequency range and deriving the primary moment. In the following, description is first given of a detection principle of the bio-optical measuring apparatus 4 and then, of a signal processing method in the signal processing unit 130.

(Detection Principle)

FIG. 23 illustrates an example of a detection principle of the bio-optical measuring apparatus 4. As illustrated in FIG. 23, inside of the living body 100, skin and inner skin lie one on top of the other from a living body surface. The light La emitted by the light source 11 enters inside of the living body 100 from the living body surface, is scattered in each layer of the skin and the inner skin, and scattered light (reflected light Lb) thereof is received by the two optical receivers 12 (12C and 12D).

The optical receiver 12D is disposed at a position where the light scattered in the inner skin is dominantly received. On the inner skin, many blood vessels, which are sources of the blood flow rate, are present. The optical receiver 12D is disposed at a position farther from the light source 11 than the optical receiver 12C. The optical receiver 12C is disposed at a position where light passing through only the skin or surface-reflected light is dominantly received and where light that reaches the inside of the living body, such as a subcutaneous tissue, is not easily received (position close to the light source 11). The optical receiver 12C is disposed at a position that is 1 mm or less from the light source 11, for example.

The optical receiver 12C and the optical receiver 12D are mounted on the same substrate 100A. Consequently, in a case where the optical path changes due to body motions or the like, it is believed that the noise due to the motions (hereinafter referred to as "motion noise") equally acts on both of the optical receiver 12C and the optical receiver 12D. From this, when the motion noise occurs, the optical receiver 12C installed in proximity to the light source 11 observes relatively less blood flow rate information and the noise signal due to the motions, and the optical receiver 11D relatively far from the light source 11 observes relatively much blood flow rate information and the noise signal due to same motions as the motions observed in the optical receiver 11C. The signal processing unit 130 obtains the low-noise signal in which the motion noise has been reduced, on the basis of the detection signals 120a obtained in the two ADCs 120.

To confirm effectiveness of a method of reducing the motion noise, a water solution in which blood-mimicking polystyrene spheres of 0.5 μm (polystyrene microsphere manufactured by Polybead Inc.) were dispersed was prepared, and phantoms (human body simulation samples) each sealed by a skin-mimicking lid made of a resin (polyacetal resin Delrin, t=2 mm, manufactured by DuPont Company) were prepared. Then, confirmation was performed. The polystyrene spheres caused Brownian movement in the water solution. Thus, an evaluation was made on the assumption that motions by the Brownian movement was the blood flow motion.

To measure behavior corresponding to an amount of the blood flow information, a test was conducted using the phantom in which pure water containing no polystyrene spheres was enclosed, mimicking conditions that the distance between the light source 11 and the optical receiver 12 was close and there was little blood flow information, or the phantom in which the polystyrene water solution was enclosed as the conditions that the distance between the light source 11 and the optical receivers 12 was far and there was much blood flow information. This phantom was installed on an electric-powered stage that ran at a fixed speed. FIG. 24 illustrates a result of measurement of a speed caused by particles carried out while changing the speed of the electric-powered stage.

From FIG. 24, in the phantom with the particles in a case where the stage remained still, a speed index attributed to the Brownian movement has been obtained. In contrast, in the phantom without particles, the speed index is 0. When the stage is moved, the speed index rises in both of the phantoms, due to the motion noise. At this time, it is seen that when the stage speed is 2 minis or faster, the speed indices behave in a substantially same manner. From this, it is seen that when the stage speed is 2 minis or faster, the motion noise behaves in the same manner, irrespective of presence or absence of the particles (that is, the blood flow).

It is to be noted that in the case of experiment conditions of this time, when the stage speed is smaller than 2 minis, a difference is seen in the speed indices, depending on presence or absence of the particles. Therefore, it is seen that estimation of the blood flow rate is possible through the use of both of the information without particles (in a case where the distance between the light source 11 and the optical receivers 12 is close) and the information with the particles (in a case where the distance between the light source 11 and the optical receivers 12 is far).

FIG. 25 and FIG. 26 each illustrate an example of the speed index measured at each of the optical receivers 12 in a case where the human body is actually measured. FIG. 25 exemplifies the speed index when the distance between the light source 11 and the optical receiver 12 is far. FIG. 26 exemplifies the speed index when the distance between the light source 11 and the optical receivers 12 is close.

It is seen from FIG. 25 that variations are seen in the blood flow volume corresponding to pulsation of the heart for 5 seconds or shorter during which there is no motion, and that offset occurs in the speed index due to the motion noise after 5 seconds during which there is a motion. In contrast, it is seen from FIG. 26 that there are small variations in the blood flow volume due to the pulsation of the heart for 5 seconds or shorter during which there is no motion, and the offset occurs in the speed index due to the motion noise after 5 seconds during which there is a motion. It is seen from the experiments using the phantoms that the offset due to the motion noise has an equivalent influence, irrespective of presence or absence of the blood flow signal. Consequently, subtraction of the signal obtained from the optical receiver 12C with the close distance from the light source 11 to the optical receiver 12 from the signal obtained from the optical receiver 12D with the far distance from the light source 11 to the optical receiver 12 makes it possible to obtain the blood flow signal in which the motion noise has been alleviated.

In practice, however, the optical receiver 12C close to the light source 11 receives more light than the optical receiver 12D receives. Consequently, it is necessary to multiply the detection signal obtained from the optical receiver 12C, the optical receiver 12D, or both by a coefficient for adjusting the amount of light, or to use optical receivers having mutually different light receiving areas as the optical receiver 12C and the optical receiver 12D. In addition, light reaches the optical receiver 12C and the optical receiver 12D through mutually different optical paths, and thus the blood flow rate information is superimposed on mutually different baselines. Consequently, to remove the motion noise, it is preferable that the signal processing unit 130 perform subtraction processing using a term for adjusting the baselines or a coefficient for adjusting signal level, as listed by the following expression (1), for example.

$$d = (S1 - B1) - K \times (S2 - B2) + B1 \qquad \text{Expression (1)}$$

d: A digital detection signal (low-noise signal) in which the motion noise has been reduced S1: A digital detection signal obtained from the optical receiver 12D B1: A digital signal of the baseline of the optical receiver 12D S2: A digital detection signal obtained from the optical receiver 12C B2: A digital signal of the baseline of the optical receiver 12C K: A coefficient for adjusting the signal level In addition, as another method of removing the motion noise, utilizing the fact that while the motion noise is equally superimposed on the optical receiver 12C and the optical receiver 12D, a ratio of the blood flow signals varies, the motion noise may be removed through the use of the statistical processing such as the principal component analysis, the singular value decomposition, or the independent component analysis, for example. For example, the signal processing unit 130 performs the principal component analysis on the detection signals 120a1 and 120a2 obtained by the respective optical receivers 12C and 12D, and extracts the first principal component from the detection signals 120a1 and 120a2. The first principal component is a signal attributed to an action of the living body. The signal processing unit 130 further generates the low-noise signal in which the motion noise has been reduced, on the basis of the statistical signal (first principal component obtained from the detection signals 120a1 and 120a2, for example) obtained by the statistical processing on the detection signals 120a1 and 120a2, for example. The signal processing unit 130 generates a direct component of the first principal component obtained from the detection signals 120a1 and 120a2, for example. The signal processing unit 130 obtains the aforementioned direct component by projecting the detection signal 120a2, for example, on an axis of the aforementioned direct component. The signal processing unit 130 generates, for example, this direct component for each predetermined time period. The signal processing unit 130 obtains the low-noise signal by, for example, performing the averaging processing using a plurality of the direct components that are generated for each predetermined time period. The signal processing unit 130 derives the power spectrum as illustrated in FIG. 4, for example, for each of differential signals, by performing the FFT on the plurality of differential signals, for example. The signal processing unit 130 further derives the averaged power spectrum as illustrated in FIG. 5, for example, by performing the averaging processing using the plurality of derived power spectra, for example.

The signal processing unit 130 derives the blood flow rate, which is the biological information of the living body 100, on the basis of the obtained low-noise signal. The signal processing unit 130 derives the blood flow rate by, for example, performing the integration on the obtained low-noise signal in the appropriate frequency range and deriving the primary moment.

[Effects]

In the following, description is given of the effects of the bio-optical measuring apparatus 4.

In the present embodiment, the subtraction processing using the aforementioned expression (1) or the aforementioned statistical processing is performed on the detection signals 120a obtained in the respective optical receivers 12C and 12D. This makes it possible to suppress the noise due to the motions in the everyday life and achieve measurement of the blood flow rate in a stable manner.

6. Modification Examples of Fourth Embodiment

In the following, description is given of modification examples of the bio-optical measuring apparatus 4 according to the aforementioned fourth embodiment.

[Modification Example F]

FIG. 27 and FIG. 28 each illustrate a modification example of the schematic configuration of the bio-optical measuring apparatus 4. A bio-optical measuring apparatus 4 according to this modification example corresponds to the bio-optical measuring apparatus 4 according to the aforementioned fifth embodiment in which a bandpass filter 15 that selectively transmits light having a desired wavelength range is provided on a light output surface of the light source 11 or on a light input surface of each of the optical receivers 12. Such a configuration makes it possible to suppress generation of noise due to unwanted outside light, and to perform highly accurate measurements, for example.

[Modification Example G]

FIG. 29 illustrates a modification example of the schematic configuration of the bio-optical measuring apparatus 4. A bio-optical measuring apparatus 4 according to this modification example corresponds to the bio-optical measuring apparatus 4 according to the aforementioned fifth embodiment in which an acceleration sensor 140 is further provided. A detection signal obtained by the acceleration sensor 140 is inputted to the signal processing unit 130. The signal processing unit 130 may sense the body motions, on the basis of the detection signal inputted from the acceleration sensor 140 and perform processing to reduce the motion noise only in a case where the body is moving. Such a configuration makes it possible to suppress the noise due to the motions in the everyday life and to achieve the measurement of the blood flow rate in a stable manner.

[Modification Example H]

FIG. 30 illustrates a modification example of the schematic configuration of the bio-optical measuring apparatus 4. A bio-optical measuring apparatus 4 according to this modification example corresponds to the bio-optical measuring apparatus 4 according to the aforementioned fifth embodiment in which four optical receivers 12 are provided and one each of the ADCs 120 is provided for each of the optical receivers 12. The signal processing unit 130 acquires a digital detection signal 120a obtained at each of the ADCs 120.

In this modification example, the optical module 110 includes the one light source 11 and the four optical receivers 12 on the substrate 110A, as illustrated in FIG. 31, for example. The substrate 110A is, for example, a wiring board that mutually and electrically couples the optical receivers 12 and the ADCs 120. The substrate 110A is also a support substrate that supports the one light source 11 and the four optical receivers 12.

The one light source 11 and the four optical receivers 12 are disposed (mounted) on the one surface of the substrate 110A, for example. The four optical receivers 12 are disposed at four locations on the substrate 110A each having the mutually different distance from the light source 11 in the predetermined direction from the light source 11. In the following, of the four optical receivers 12, the optical receiver 12 closest to the light source 11 is referred to as the optical receiver 12C, the optical receiver 12 second closest to the light source 11 is referred to as the optical receiver 12E, the optical receiver 12 third closest to the light source 11 is referred to as the optical receiver 12D, and the optical receiver 12 fourth closest to the light source 11 is referred to as the optical receiver 12F.

The respective optical receivers 12 receive reflected light Lb from the living body 100, of the light outputted from the light source 11 toward the living body 100. That is, the respective optical receivers 12 are disposed at positions where the reflected light Lb from the living body 100 is receivable, of the light outputted from the light source 11 toward the living body 100. The reflected light Lb corresponds to the light that is outputted from the light source 11 and back scattered by the living body 100. When the reflected light Lb from the living body 100 is inputted, the respective optical receivers 12 output detection signals corresponding to the inputted reflected light Lb. When reflected light Lb (Lb1) from the living body 100 is inputted, the optical receiver 12C outputs a detection signal 12c1 corresponding to the inputted reflected light Lb (Lb1). When reflected light Lb (Lb2) from the living body 100 is inputted, the optical receiver 12D outputs a detection signal 12d1 corresponding to the inputted reflected light Lb (Lb2). When reflected light Lb (Lb3) is inputted from the living body 100, the optical receiver 12E outputs a detection signal 12e1 corresponding to the inputted reflected light Lb (Lb3). When reflected light Lb (Lb4) is inputted from the living body 100, the optical receiver 12F outputs a detection signal 12f1 corresponding to the input reflected light Lb (Lb4).

The ADCs 120 convert the detection signals inputted from the optical receivers 12 from the analog signal to the digital signal and output the detection signals as the digital detection signals 120a to the signal processing unit 130. When the detection signal is inputted from the optical receiver 12C, the corresponding ADC 120 coupled to the optical receiver 12C outputs the digital detection signal 120a (120a1). When the detection signal is inputted from the optical receiver 12D, the corresponding ADC 120 coupled to the optical receiver 12D outputs the digital detection signal 120a (120a2). When the detection signal is inputted from the optical receiver 12E, the corresponding ADC 120 coupled to the optical receiver 12E outputs a digital detection signal 120a (120a3). When the detection signal is inputted from the optical receiver 12F, the corresponding ADC 120 coupled to the optical receiver 12F outputs a digital detection signal 120a (120a4).

The signal processing unit 130 performs the control of light emission of the light source 11 or the control of light reception of the respective optical receivers 12. The signal processing unit 130 further derives the blood flow rate by processing the detection signals 120a inputted from the respective ADCs 120. The signal processing unit 130 obtains the low-noise signal, on the basis of the detection signals 120a obtained by the four ADCs 120. The signal processing unit 130 derives the blood flow rate, which is the biological information of the living body 100, on the basis of the obtained low-noise signal. The signal processing circuit 130 derives the blood flow rate by, for example, performing the integration on the obtained low-noise signal in the appropriate frequency range and deriving the primary moment.

It is preferable that the signal processing unit 130 perform the subtraction processing using the term for adjusting the baselines or the coefficient for adjusting the signal level, as listed by the following expressions (2) and (3), for example.

$$d1 = (S1 - B1) - K1 \times (S2 - B2) + B1 \quad \text{Expression (2)}$$

$$d2 = (S3 - B3) - K2 \times (S4 - B4) + B3 \quad \text{Expression (3)}$$

d1: A digital detection signal (low-noise signal) in which the motion noise has been reduced d2: A digital detection signal (low-noise signal) in which the motion noise has been reduced S1: A digital detection signal obtained from the optical receiver 12D B1: A digital signal of the baseline of the optical receiver 12D S2: A digital detection signal obtained from the optical receiver 12C B2: A digital signal of the baseline of the optical receiver 12C K1: A coefficient for adjusting the signal level S3: A digital detection signal obtained from the optical receiver 12F B3: A digital signal of the baseline of the optical receiver 12F S4: A digital detection signal obtained from the optical receiver 12E B5: A digital signal of the baseline of the optical receiver 12E K2: A coefficient for adjusting the signal level In addition, the signal processing unit 130 performs the principal component analysis on the detection signals 120a1 and 120a2 obtained by the respective optical receivers 12C and 12D, for example, and extracts the first principal component from the detection signals 120a1 and 120a2. The first principal component is the signal attributed to the action of the living body. The signal processing unit 130 further generates the low-noise signal in which the motion noise has been reduced, on the basis of the statistical signal (first principal component obtained from the detection signals 120a1 and 120a2, for example) obtained by the statistical processing on the detection signals 120a1 and 120a2, for example. The signal processing unit 130 generates a direct component of the first principal component obtained from the detection signals 120a1 and 120a2, for example. The signal processing unit 130 obtains the aforementioned direct component by projecting the detection signal 120a2, for example, on the axis of the aforementioned direct component. The signal processing unit 130 generates, for example, this direct component for each predetermined time period. The signal processing unit 130 obtains the low-noise signal by, for example, performing the averaging processing using a plurality of the direct components that are generated for each predetermined time period. The signal processing unit 130 derives the power spectrum as illustrated in FIG. 4, for example, for each of the differential signals, by performing the FFT on the plurality of differential signals, for example. The signal processing unit 130 further derives the averaged power spectrum as illustrated in FIG. 5, for example, by performing the averaging processing using the plurality of derived power spectra, for example.

Furthermore, the signal processing unit 130 performs the principal component analysis on the detection signals 120a3 and 120a4 obtained by the respective optical receivers 12E and 12F, for example, and extracts the first principal component from the detection signals 120a3 and 120a4. The first principal component is the signal attributed to the action of the living body. The signal processing unit 130 further generates the low-noise signal in which the motion noise has been reduced, on the basis of the statistical signal (first principal component obtained from the detection signals 120a3 and 120a4, for example) obtained by the statistical processing on the detection signals 120a3 and 120a4, for example. The signal processing unit 130 generates a direct component of the first principal component obtained from the detection signals 120a3 and 120a4, for example. The signal processing unit 130 obtains the aforementioned direct component by projecting the detection signal 120a4, for example, on the axis of the aforementioned direct component. The signal processing unit 130 generates, for example, this direct component for each predetermined time period. The signal processing unit 130 obtains the low-noise signal by, for example, performing the averaging processing using a plurality of the direct components that are generated for each predetermined time period. The signal processing unit 130 derives the power spectrum as illustrated in FIG. 4, for example, for each of the differential signals, by performing the FFT on the plurality of differential signals, for example. The signal processing unit 130 further derives the averaged power spectrum as illustrated in FIG. 5, for example, by performing the averaging processing using the plurality of derived power spectra, for example.

Incidentally, the ratios of the blood flow signals of the low-noise signal obtained on the basis of the respective detection signals 120a1 and 120a2 and the low-noise signal obtained on the basis of the respective detection signals 120a3 and 120a4 are mutually different. Then, the signal processing unit 130 derives the blood flow rate, which is the biological information of the living body 100, on the basis of the two low-noise signals. The signal processing unit 130 derives the blood flow rate by, for example, performing the integration on the obtained low-noise signals in the appropriate frequency range and deriving the primary moment. By doing so, it is possible to achieve the measurement of the blood flow rate with even higher accuracy than the accuracy in the aforementioned fourth embodiment.

It is to be noted that, in this modification example, the number of the optical receivers 12 may be 6 or more. In addition, in this modification example, the optical receivers 12D and 12F may be disposed side by side in a direction intersecting an arrangement direction of the optical receivers 12C and 12E. For example, as illustrated in FIG. 32, in this modification example, the optical receivers 12D and 12F may be disposed side by side in a direction orthogonal to the arrangement direction of the optical receivers 12C and 12E. Even in such a case, it is possible to achieve the measurement of the blood flow rate with even higher accuracy than the accuracy in the aforementioned fourth embodiment.

[Modification Example I]

In the aforementioned fourth embodiment and the modification examples thereof, the signal processing unit 130 may perform the motion noise reduction processing based on the detection signals 120 obtained from the respective optical receivers 12, with a calculation method that is different from the aforementioned calculation method.

FIG. 33 illustrates an example of the change with time in the speed index obtained from the detection signals 120a1 and 120a3 that are obtained by the optical receiver 12C or the optical receiver 12E in the aforementioned fourth embodiment and the modification examples thereof. In FIG. 33, a horizontal axis represents time and a vertical axis represents a speed index D1. A speed change derived from the pulsation is seen in FIG. 33. In FIG. 33, there is the action of the living body for a certain period of time, which results in offset on the speed index D1. FIG. 34 illustrates an example of a change with time of a standard deviation D2 per unit time of the detection signals 120a2 and 120a4 that are obtained from the optical receiver 12D or the optical receiver 12F in the aforementioned fourth embodiment and the modification examples thereof. In FIG. 34, the horizontal axis represents the time, and the vertical axis represents the standard deviation D2 per unit time of the detection signals 120a2 and 120a4. In FIG. 34, in a certain period of time, there is the action of the living body which results in offset on the standard deviation D2.

FIG. 35 illustrates an example of a relation between the standard deviation D2 of FIG. 34 and the speed index D1 of FIG. 33. It is seen from FIG. 35 that it is possible to approximate the relation between the standard deviation D2 of FIG. 34 and the speed index D1 of FIG. 33 with an approximation expression f (D2), such as a second degree equation or a third or higher degree equation. FIG. 36 illustrates an example of a change with time of the speed index D1 of FIG. 33 in which the motion noise has been reduced by means of the approximation expression f(D2) that derives the speed index with the standard deviation D2 as a parameter (D1−f (D2)), and of the speed index D1 of FIG. 33. It is seen from FIG. 36 that in D1−f(D2), although the speed change derived from the pulsation has attenuated, the offset generated by the action of the living body is suppressed.

Then, in this modification example, the signal processing unit 130 obtains the low-noise signal on the basis of the speed index D1 (first speed index) obtained from the detection signal 120a1 or the detection signal 120a3 and the standard deviation D2 obtained from the detection signal 120a2 or the detection signal 120a4. The signal processing unit 130 obtains the low-noise signal on the basis of the speed index D1 and the approximation expression f(D2), for example. The signal processing unit 130 derives a speed index (second speed index) from the standard deviation D2 by means of the approximation expression f(D2), for example, and obtains the low-noise signal on the basis of the speed index D1 (hereinafter referred to as "D1'") obtained from the detection signal 120a1 or the detection signal 120a3, and a speed index (hereinafter referred to as "D1'''") obtained from the approximation expression f(D2). The signal processing unit 130 derives a difference (D1'−D1") between the speed index D1' and the speed index D1", for example, and makes a signal (differential signal) thereby obtained the low-noise signal.

The signal processing unit 130 derives the blood flow rate, which is the biological information of the living body 100, on the basis of the obtained low-noise signal, for example. The signal processing unit 130 derives the blood flow rate by, for example, performing the integration on the obtained low-noise signal in the appropriate frequency range and deriving the primary moment.

In this manner, in this modification example, the low-noise signal is obtained on the basis of the speed index D1 and the approximation expression f(D2). This makes it possible to suppress the noise due to the motions in the everyday life and to achieve the measurement of the blood flow rate in a stable manner.

It is to be noted that the signal processing unit 130 may derive an index representative of variations per unit time (hereinafter referred to as a "variation index") of the detection signals 120a2 and 120a4 obtained from the optical receiver 12D or the optical receiver 12F in the aforementioned fourth embodiment and the modification examples thereof, instead of deriving the standard deviation D2 per unit time of the detection signals 120a2 and 120a4 obtained from the optical receiver 12D or the optical receiver 12F in the aforementioned fourth embodiment and the modification examples thereof, for example. Even in such a case, the low-noise signal is obtained on the basis of the speed index D1 and the approximation expression f(D2). Therefore, it is possible to suppress the noise due to the motions in the everyday life and achieve the measurement of the blood flow rate in a stable manner.

It is to be noted that the effects described herein are merely illustrative. The effects of the present disclosure are not limited to the effects described herein. The present disclosure may have any effects other than the effects described herein.

Moreover, the present disclosure may have the following configurations, for example.

(1)

A bio-optical measuring apparatus including:

a light source that emits coherent light;

three or more optical receivers that receive reflected light from a living body, of light outputted from the light source toward the living body; and a signal processing unit that obtains a low-noise signal, by performing averaging processing based on detection signals outputted from the respective optical receivers, in response to reception of the reflected light.

(2)

The bio-optical measuring apparatus according to (1), in which the signal processing unit obtains the low-noise signal by generating, on a basis of the respective detection signals, first correction signals in which in-phase noise has been reduced and the number of which is larger than half of the number of the optical receivers, and by performing the averaging processing using the plurality of generated first correction signals.

(3)

The bio-optical measuring apparatus according to (2), in which the signal processing unit obtains the respective first correction signals by making the detection signal a reference signal, the detection signal being outputted from the one optical receiver of the three or more optical receivers, and by deriving differences between the reference signal and the respective detection signals, excluding the reference signal, of the detection signals outputted from the respective optical receivers.

(4)

The bio-optical measuring apparatus according to (3), in which the respective optical receivers are disposed at positions each having a distance from the light source that is substantially equal to each other.

(5)

The bio-optical measuring apparatus according to (3), in which the plurality of optical receivers is disposed in matrix at positions adjacent to the light source, and the signal processing unit obtains the respective first correction signals on the basis of respective second correction signals obtained by performing correction on the respective detection signals, the correction corresponding to a distance from the light source, of the optical receiver from which the detection signal has been obtained.

(6)

The bio-optical measuring apparatus according to (2), in which the signal processing unit obtains the respective first correction signals by making one of the three or more second correction signals a reference signal, and by deriving differences between the reference signal and the respective detection signals, excluding the reference signal, of the three or more second correction signals.

(7)

The bio-optical measuring apparatus according to (5), in which the plurality of optical receivers includes one image sensor.

(8)

The bio-optical measuring apparatus according to any one of (1) to (7), in which the signal processing unit calculates a blood flow rate on the basis of a beat signal that is included in the low-noise signal and generated by a laser Doppler.

(9)

A bio-optical measuring apparatus including:

a light source that emits coherent light;

two or more first optical receivers that receive first reflected light from a living body, of light outputted from the light source toward the living body;

a reflective plate that reflects the light outputted from the light source;

a second optical receiver that receives second reflected light reflected by the reflective plate, of the light outputted from the light source; and a signal processing unit that obtains a low-noise signal by performing averaging processing based on first detection signals and a second detection signal, the first detection signals being outputted from the respective first optical receivers in response to reception of the first reflected light, the second detection signal being outputted from the second optical receiver in response to reception of the second reflected light.

(10)

The bio-optical measuring apparatus according to (9), in which the signal processing unit obtains the low-noise signal by generating, on the basis of the respective first detection signals and the second detection signal, correction signals in which in-phase noise has been reduced and the number of which is same as the number of the first optical receivers, and by performing the averaging processing using the plurality of generated correction signals.

(11)

The bio-optical measuring apparatus according to (10), in which the signal processing unit obtains the respective first correction signals by deriving differences between the second detection signal and the respective first detection signals.

(12)

The bio-optical measuring apparatus according to any one of (9) to (11), in which the signal processing unit calculates a blood flow rate on the basis of a beat signal that is included in the low-noise signal and generated by a laser Doppler.

(13)

A bio-optical measuring apparatus including:

a light source that emits coherent light;

two or more first optical receivers that receive reflected light from a living body, of light outputted from the light source toward the living body;

a light-shielding plate that blocks transmission of the light outputted from the light source;

a second optical receiver into which entry of light from the light source is blocked by the light-shielding plate; and a signal processing unit that obtains a low-noise signal by performing averaging processing based on first detection signals and a second detection signal, the first detection signals being outputted from the respective first optical receivers in response to reception of the reflected light, the second detection signal being outputted from the second optical receiver.

(14)

The bio-optical measuring apparatus according to (13), in which the signal processing unit obtains the low-noise signal by generating, on the basis of the respective first detection signals and the second detection signal, correction signals in which in-phase noise has been reduced and the number of which is same as the number of the first optical receivers, and by performing the averaging processing using the plurality of generated correction signals.

(15)

The bio-optical measuring apparatus according to (13) or (14), in which the signal processing unit obtains the respective first correction signals by deriving differences between the second detection signal and the respective first detection signals.

(16)

The bio-optical measuring apparatus according to any one of (13) to (15), in which the signal processing unit calculates a blood flow rate on the basis of a beat signal that is included in the low-noise signal and generated by a laser Doppler.

(17)

A bio-optical measuring apparatus including:

a light source that emits coherent light;

two or more optical receivers that receive reflected light from a living body, of light outputted from the light source toward the living body; and a signal processing unit that obtains a low-noise signal by performing averaging processing based on detection signals and a statistical signal, the detection signals being outputted from the respective optical receivers in response to reception of the reflected light, the statistical signal being obtained by performing statistical processing using the respective detection signals.

(18)

The bio-optical measuring apparatus according to (17), in which the signal processing unit obtains the low-noise signal by generating, on the basis of the respective detection signals and the statistical signal, correction signals in which in-phase noise has been reduced and the number of which is same as the number of the optical receivers, and by performing the averaging processing using the plurality of generated correction signals.

(19)

The bio-optical measuring apparatus according to (18), in which the statistical processing is a principal component analysis, singular value decomposition, or an independent component analysis.

(20)

The bio-optical measuring apparatus according to any one of (17) to (19), in which the signal processing unit calculates a blood flow rate on the basis of a beat signal that is included in the low-noise signal and generated by a laser Doppler.

(21)

A bio-optical measuring apparatus including:

a light source that emits coherent light;

two or more optical receivers that receive reflected light from a living body, of light outputted from the light source toward the living body; and a signal processing unit that obtains a low-noise signal by performing processing to reduce noise due to motions of the living body, on the basis of detection signals outputted from the respective optical receivers in response to reception of the reflected light.

(22)

The bio-optical measuring apparatus according to (21), in which the respective optical receivers are disposed at positions each having a mutually different distance from the light source.

(23)

The bio-optical measuring apparatus according to (21) or (22), in which the signal processing unit obtains the low-noise signal by using the following expression:

$$d=(S1-B1)-K\times(S2-B2)+B1, \text{ where}$$

d: the low-noise signal;

S1: the detection signal obtained from the optical receiver that is relatively close to the light source;

B1: a signal of a baseline of the optical receiver that outputs S1;

S2: the detection signal obtained from the optical receiver that is relatively far from the light source;

B2: a signal of a baseline of the optical receiver that outputs S2; and

K: a coefficient for adjusting signal level.

(24)

The bio-optical measuring apparatus according to (21) or (22), in which the signal processing unit obtains the low-noise signal on the basis of a first speed index and a standard deviation per unit time, the first speed index being obtained on the basis of the detection signal obtained from the optical receiver that is relatively close to the light source, the standard deviation being of the detection signal obtained from the optical receiver that is relatively far from the light source.

(25)

The bio-optical measuring apparatus according to (24), in which the signal processing unit obtains the low-noise signal by deriving a difference between the first speed index and a second speed index, the second speed index being obtained from an approximation expression that derives a speed index with the standard deviation as a parameter.

(26)

The bio-optical measuring apparatus according to any one of (21) to (25), in which the plurality of optical receivers includes one image sensor.

(27)

The bio-optical measuring apparatus according to any one of (21) to (26), in which the signal processing unit calculates a blood flow rate on the basis of a beat signal that is included in the low-noise signal and generated by a laser Doppler.

This application claims the benefits of Japanese Priority Patent Application JP2017-159972 filed with the Japan Patent Office on Aug. 23, 2017, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof

What is claimed is:

1. A bio-optical measuring apparatus comprising:
  a light source configured to emit coherent light towards a living body;
  a plurality of optical receivers configured to receive reflected light from the living body; and
  a signal processing unit configured to: generate, based on respective detection signals received for each of the plurality of optical receivers, a plurality of first correction signals in which in-phase noise has been reduced, wherein a number of the plurality of first correction signals is larger than half of a number of the plurality of optical receivers; and
  obtain a low noise signal by performing averaging processing using the plurality of first correction signals.

2. The bio-optical measuring apparatus according to claim 1, wherein the signal processing unit is configured to obtain the plurality of first correction signals by making one of the respective detection signals a reference signal, and by deriving differences between the reference signal and remaining ones of the respective detection signals, excluding the reference signal.

3. The bio-optical measuring apparatus according to claim 2, wherein the plurality of optical receivers are disposed at positions each having a distance from the light source that is substantially equal to each other.

4. The bio-optical measuring apparatus according to claim 2,
wherein the plurality of optical receivers are disposed in a matrix at positions adjacent to the light source, and
wherein the signal processing unit is configured to obtain the plurality of first correction signals on a basis of a plurality of second correction signals obtained by performing a correction on the respective detection signals, the correction corresponding to a distance from the light source, of each optical receiver from which a detection signal has been obtained.

5. The bio-optical measuring apparatus according to claim 4, wherein the signal processing unit is configured to obtain the plurality of first correction signals by making one of the plurality of second correction signals a reference signal, and by deriving differences between the reference signal and remaining ones of the respective detection signals, excluding the reference signal.

6. The bio-optical measuring apparatus according to claim 1, wherein the plurality of optical receivers includes one image sensor.

7. The bio-optical measuring apparatus according to claim 1, wherein the signal processing unit is configured to calculate a blood flow rate on a basis of a beat signal generated by a laser Doppler.

8. A bio-optical measuring apparatus comprising:
a light source configured to emit coherent light;
two or more first optical receivers configured to receive first reflected light from a living body;
a reflective plate configured to reflect the light outputted from the light source;
a second optical receiver configured to receive second reflected light reflected by the reflective plate, of the light outputted from the light source; and
a signal processing unit configured to obtain a low-noise signal by performing averaging processing based on first detection signals and a second detection signal, the first detection signals being outputted from the respective first optical receivers in response to reception of the first reflected light, the second detection signal being outputted from the second optical receiver in response to reception of the second reflected light, wherein the signal processing unit is configured to obtain the low-noise signal by generating, on a basis of the respective first detection signals and the second detection signal, a plurality of correction signals in which in-phase noise has been reduced and a number of which is equal to a number of the first optical receivers, and by performing the averaging processing using the plurality of generated correction signals.

9. The bio-optical measuring apparatus according to claim 8, wherein the signal processing unit is configured to obtain the respective correction signals by deriving differences between the second detection signal and the respective first detection signals.

10. The bio-optical measuring apparatus according to claim 8, wherein the signal processing unit is configured to calculate a blood flow rate on a basis of a beat signal that is included in the low-noise signal and generated by a laser Doppler.

11. A bio-optical measuring apparatus comprising:
a light source configured to emit coherent light;
two or more first optical receivers configured to receive reflected light from a living body;
a light-shielding plate configured to block transmission of the light outputted from the light source;
a second optical receiver into which entry of light from the light source is blocked by the light-shielding plate; and
a signal processing unit configured to obtain a low-noise signal by performing averaging processing based on first detection signals and a second detection signal, the first detection signals being outputted from the respective first optical receivers in response to reception of the reflected light, the second detection signal being outputted from the second optical receiver, wherein the signal processing unit is configured to obtain the low-noise signal by generating, on a basis of the respective first detection signals and the second detection signal, a plurality of correction signals in which in-phase noise has been reduced and a number of which is equal to a number of the first optical receivers, and by performing the averaging processing using the plurality of generated correction signals.

12. The bio-optical measuring apparatus according to claim 11, wherein the signal processing unit is configured to obtain the respective correction signals by deriving differences between the second detection signal and the respective first detection signals.

13. The bio-optical measuring apparatus according to claim 11, wherein the signal processing unit is configured to calculate a blood flow rate on a basis of a beat signal that is included in the low-noise signal and generated by a laser Doppler.

14. A bio-optical measuring apparatus comprising:
a light source configured to emit coherent light;
two or more optical receivers configured to receive reflected light from a living body; and
a signal processing unit configured to obtain a low-noise signal by performing averaging processing based on detection signals and a statistical signal, the detection signals being outputted from the respective optical receivers in response to reception of the reflected light, the statistical signal being obtained by performing statistical processing using the respective detection signals, wherein the signal processing unit is configured to obtain the low-noise signal by generating, on a basis of the respective detection signals and the statistical signal, a plurality of correction signals in which in-phase noise has been reduced and a number of which is equal to a number of the optical receivers, and by performing the averaging processing using the plurality of generated correction signals.

15. The bio-optical measuring apparatus according to claim 14, wherein the statistical processing is a principal component analysis, singular value decomposition, or an independent component analysis.

16. The bio-optical measuring apparatus according to claim 14, wherein the signal processing unit is configured to calculate a blood flow rate on a basis of a beat signal that is included in the low-noise signal and generated by a laser Doppler.

* * * * *